(12) United States Patent
Simmonds et al.

(10) Patent No.: US 7,073,220 B2
(45) Date of Patent: Jul. 11, 2006

(54) BED SIDERAIL HAVING A LATCH

(75) Inventors: Scott Simmonds, Greensburg, IN (US);
Brent Goodwin, Middletown, OH (US); James K. Findlay, Fishers, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 22 days.

(21) Appl. No.: 10/811,182

(22) Filed: Mar. 26, 2004

(65) Prior Publication Data

US 2004/0177443 A1 Sep. 16, 2004

Related U.S. Application Data

(63) Continuation-in-part of application No. 10/657,696, filed on Sep. 8, 2003.

(60) Provisional application No. 60/490,467, filed on Jul. 28, 2003, provisional application No. 60/489,171, filed on Jul. 22, 2003, provisional application No. 60/458,720, filed on Mar. 28, 2003, provisional application No. 60/409,748, filed on Sep. 11, 2002, provisional application No. 60/408,698, filed on Sep. 6, 2002.

(51) Int. Cl.
*A47C 21/08* (2006.01)
*E05C 1/12* (2006.01)
(52) U.S. Cl. ................. 5/428; 5/430; 5/425; 292/36
(58) Field of Classification Search ............ 5/424–430, 5/100, 662; 292/32, 34–37, 41, 139, 156, 292/159, 165, 167
See application file for complete search history.

(56) References Cited

U.S. PATENT DOCUMENTS

| 164,534 | A | * | 6/1875 | Du Four ................. 49/193 |
| 405,784 | A | * | 6/1889 | Livingstone ............ 292/37 |
| 406,903 | A | * | 7/1889 | Hebert .................. 292/34 |
| 412,356 | A | * | 10/1889 | Zerfas et al. ........... 292/33 |
| 421,656 | A | | 2/1890 | Blanken ................. 5/425 |
| 966,063 | A | * | 8/1910 | Toothaker .............. 292/36 |
| 993,119 | A | | 5/1911 | Stannard ................ 5/512 |
| 1,006,211 | A | * | 10/1911 | Hermon ................ 292/36 |
| 1,089,941 | A | * | 3/1914 | Mlley ................... 292/36 |
| 1,174,652 | A | * | 3/1916 | Banks .................. 292/36 |
| 1,294,399 | A | * | 2/1919 | Chappelle .............. 70/118 |
| 1,319,011 | A | * | 10/1919 | Kuretich ............... 292/36 |
| 1,398,203 | A | | 11/1921 | Schmidt ................ 5/618 |
| 1,593,435 | A | * | 7/1926 | Carter ................. 292/36 |
| 1,671,249 | A | * | 5/1928 | Lieberman ............. 70/118 |
| 1,824,866 | A | * | 9/1931 | Bristol ................. 92/23 |
| 2,136,088 | A | | 11/1938 | Stevens ................ 55/429 |

(Continued)

FOREIGN PATENT DOCUMENTS

DE 199 00 602 C1 7/2000

(Continued)

OTHER PUBLICATIONS

"Paramount Bed" brochure in Japanese; 63 pages.

(Continued)

*Primary Examiner*—Robert G. Santos
(74) *Attorney, Agent, or Firm*—Bose McKinney & Evans LLP

(57) ABSTRACT

A patient support including a frame, a mattress supported by the frame, and siderails supported by the frame. A latch member is configured to prevent vertical movement of the siderail. A latch position indicator is configured to provide an indication of the position of the latch member.

15 Claims, 15 Drawing Sheets

U.S. PATENT DOCUMENTS

| | | | |
|---|---|---|---|
| 2,164,484 A | 7/1939 | Wolfe | 5/425 |
| 2,254,466 A | 9/1941 | Albert | 297/225 |
| 2,281,209 A | 4/1942 | Smith | 5/618 |
| 2,452,366 A | 10/1948 | Freund | 5/624 |
| 2,556,591 A | 6/1951 | Loxley | 5/618 |
| 2,560,459 A * | 7/1951 | Lungberg et al. | 292/35 |
| 2,564,083 A | 8/1951 | Stechert | 5/618 |
| 2,587,291 A | 2/1952 | Des Rochers | 5/430 |
| 2,605,151 A | 7/1952 | Shampaine | 5/602 |
| 2,644,173 A | 7/1953 | James | 5/425 |
| 2,710,976 A | 6/1955 | Martensen | 5/84.1 |
| 2,722,017 A | 11/1955 | Burst et al. | 5/428 |
| 2,734,104 A | 2/1956 | Gollhofer | 200/61.75 |
| 2,766,463 A | 10/1956 | Bendersky | 5/623 |
| 2,817,854 A | 12/1957 | Pratt | 5/428 |
| 2,817,855 A | 12/1957 | Pratt | 5/428 |
| 2,869,614 A | 1/1959 | Wamsley | 280/230 |
| 2,951,252 A | 9/1960 | Roche | 5/279.1 |
| 3,010,121 A | 11/1961 | Breach | 5/618 |
| 3,018,492 A | 1/1962 | Rosen | 5/93.1 |
| 3,021,534 A | 2/1962 | Hausted | 5/430 |
| 3,053,568 A | 9/1962 | Miller | 297/78 |
| 3,055,020 A | 9/1962 | Mann | 5/430 |
| 3,099,440 A | 7/1963 | Burzlaff | 5/614 |
| 3,104,402 A | 9/1963 | Johnson | 5/428 |
| 3,112,500 A | 12/1963 | MacDonald | 5/618 |
| 3,138,805 A | 6/1964 | Piazza | 5/618 |
| 3,148,387 A | 9/1964 | Samie, Jr., et al. | 5/632 |
| 3,197,852 A | 8/1965 | Johnson | 29/446 |
| 3,210,779 A | 10/1965 | Herbold | 5/610 |
| 3,220,021 A | 11/1965 | Nelson | 5/618 |
| 3,220,022 A | 11/1965 | Nelson | 5/618 |
| 3,233,255 A | 2/1966 | Propst | 5/610 |
| 3,234,570 A | 2/1966 | Hutt | 5/430 |
| 3,239,853 A | 3/1966 | MacDonald | 5/616 |
| 3,249,387 A | 5/1966 | Pivacek | 297/411.33 |
| 3,256,533 A | 6/1966 | Michelsen | 5/53.1 |
| 3,266,545 A | 8/1966 | Kruissink | 297/228.12 |
| 3,309,717 A | 3/1967 | Black | 5/618 |
| 3,321,779 A | 5/1967 | Kaufman et al. | 5/93.1 |
| 3,344,445 A | 10/1967 | Crawford | 5/430 |
| 3,351,962 A | 11/1967 | Dodrill et al. | 5/429 |
| 3,406,772 A | 10/1968 | Ahrent et al. | 180/9.23 |
| 3,456,269 A | 7/1969 | Goodman | 5/618 |
| 3,486,176 A | 12/1969 | Murcott | 5/428 |
| 3,506,989 A | 4/1970 | Ross et al. | 5/430 |
| 3,526,008 A | 9/1970 | Pruim | 5/430 |
| 3,545,799 A * | 12/1970 | Gertsfeld | 292/34 |
| 3,585,659 A | 6/1971 | Burst et al. | 5/430 |
| 3,590,403 A * | 7/1971 | Mixon | 5/100 |
| 3,593,350 A | 7/1971 | Knight et al. | 5/616 |
| 3,610,685 A | 10/1971 | Lay | 297/230.12 |
| 3,619,824 A | 11/1971 | Doyle | 5/143 |
| 3,640,566 A | 2/1972 | Hodge | 297/68 |
| 3,742,530 A | 7/1973 | Clark | 5/482 |
| 3,806,109 A | 4/1974 | Weber et al. | 5/610 |
| 3,845,511 A | 11/1974 | Benoit et al. | 5/53.1 |
| 3,851,345 A | 12/1974 | Benoit et al. | 5/429 |
| 3,865,434 A | 2/1975 | Sully | 297/411.33 |
| 3,877,090 A | 4/1975 | Schutz | 5/93.1 |
| 3,893,197 A | 7/1975 | Ricke | 5/651 |
| 3,897,973 A | 8/1975 | Long et al. | 297/75 |
| 3,905,591 A | 9/1975 | Schorr et al. | 5/601 |
| 3,916,461 A | 11/1975 | Kerstholt | 5/618 |
| 3,932,903 A | 1/1976 | Adams et al. | 5/100 |
| 3,971,083 A | 7/1976 | Peterson | 5/430 |
| 4,103,376 A | 8/1978 | Benoit et al. | 5/430 |
| 4,127,906 A | 12/1978 | Zur | 5/615 |
| 4,139,917 A | 2/1979 | Fenwick | 5/602 |
| 4,142,259 A * | 3/1979 | Moore | 4/661 |
| 4,168,099 A | 9/1979 | Jacobs et al. | 297/325 |
| 4,183,015 A | 1/1980 | Drew et al. | 340/825.19 |
| 4,186,456 A | 2/1980 | Huempfner | 5/42.8 |
| 4,214,326 A | 7/1980 | Spann | 5/632 |
| 4,215,446 A | 8/1980 | Mahoney | 5/425 |
| 4,231,030 A | 10/1980 | Weiss | 340/686.1 |
| 4,232,415 A | 11/1980 | Webber | 5/427 |
| 4,240,169 A | 12/1980 | Roos | 5/613 |
| 4,257,647 A * | 3/1981 | Gianessi | 297/336 |
| 4,258,445 A | 3/1981 | Zur | 5/614 |
| 4,312,500 A | 1/1982 | Janssen | 5/618 |
| 4,336,621 A | 6/1982 | Schwartz et al. | 5/658 |
| 4,362,328 A * | 12/1982 | Tacheny et al. | 292/36 |
| 4,370,765 A | 2/1983 | Webber | 5/427 |
| 4,409,695 A | 10/1983 | Johnston et al. | 5/601 |
| 4,435,862 A | 3/1984 | King et al. | 5/611 |
| 4,439,880 A | 4/1984 | Koncelik et al. | 5/429 |
| 4,453,732 A | 6/1984 | Assanah et al. | 280/648 |
| D276,112 S | 10/1984 | Ferrell et al. | D6/503 |
| 4,477,935 A | 10/1984 | Griffin | 5/241 |
| 4,484,367 A | 11/1984 | Jenkins | 5/425 |
| 4,525,885 A | 7/1985 | Hunt et al. | 5/713 |
| 4,527,298 A | 7/1985 | Moulton | 5/615 |
| 4,557,471 A | 12/1985 | Pazzini | 5/618 |
| 4,607,402 A | 8/1986 | Pollard | 5/425 |
| 4,612,679 A | 9/1986 | Mitchell | 5/425 |
| 4,653,129 A | 3/1987 | Kuck et al. | 5/430 |
| 4,654,903 A | 4/1987 | Chubb et al. | 5/607 |
| 4,670,923 A | 6/1987 | Gabriel et al. | 5/424 |
| 4,672,698 A | 6/1987 | Sands | 5/424 |
| 4,675,926 A | 6/1987 | Lindblom et al. | 5/618 |
| 4,676,687 A | 6/1987 | Koffler | 403/386 |
| 4,680,790 A | 7/1987 | Packard et al. | 379/432 |
| 4,685,159 A | 8/1987 | Oetiker | 5/608 |
| 4,704,750 A | 11/1987 | Wheelock | 5/127 |
| 4,710,049 A | 12/1987 | Chang | 403/23 |
| 4,710,992 A | 12/1987 | Falwell et al. | 5/663 |
| 4,745,647 A | 5/1988 | Goodwin | 5/713 |
| 4,747,171 A | 5/1988 | Einsele et al. | 5/425 |
| 4,751,754 A | 6/1988 | Bailey et al. | 5/611 |
| 4,752,977 A * | 6/1988 | Smith et al. | 5/93.1 |
| 4,767,419 A | 8/1988 | Fattore | 5/659 |
| 4,768,249 A | 9/1988 | Goodwin | 5/713 |
| 4,783,864 A | 11/1988 | Turner | 5/424 |
| 4,800,600 A | 1/1989 | Baum | 5/93.1 |
| 4,825,486 A | 5/1989 | Kimura et al. | 5/713 |
| 4,827,545 A | 5/1989 | Arp | 5/424 |
| 4,839,933 A | 6/1989 | Plewright et al. | 5/86.1 |
| 4,858,260 A | 8/1989 | Failor et al. | 5/618 |
| 4,862,529 A | 9/1989 | Peck | 5/611 |
| 4,862,530 A | 9/1989 | Chen | 5/618 |
| 4,872,228 A | 10/1989 | Bishop | 5/425 |
| 4,873,734 A | 10/1989 | Pollard | 5/425 |
| 4,892,338 A * | 1/1990 | Weinerman et al. | 292/35 |
| 4,894,876 A | 1/1990 | Fenwick | 5/602 |
| 4,912,787 A | 4/1990 | Bradcovich | 5/601 |
| 4,914,760 A | 4/1990 | Hargest et al. | 5/689 |
| 4,926,457 A | 5/1990 | Poehner et al. | 378/209 |
| 4,941,221 A | 7/1990 | Kanzler | 5/615 |
| 4,944,055 A | 7/1990 | Shainfeld | 5/618 |
| 4,951,032 A | 8/1990 | Langsam | 340/522 |
| 4,974,905 A | 12/1990 | Davis | 297/377 |
| 4,985,946 A | 1/1991 | Foster et al. | 5/601 |
| 4,987,623 A | 1/1991 | Stryker et al. | 5/86.1 |
| 4,993,089 A | 2/1991 | Solomon et al. | 5/430 |
| 4,993,920 A | 2/1991 | Harkeroad et al. | 417/44.2 |
| 4,998,939 A | 3/1991 | Potthast et al. | 5/424 |
| 5,010,611 A | 4/1991 | Mallett | 5/497 |
| 5,029,352 A | 7/1991 | Hargest et al. | 5/689 |
| 5,035,014 A | 7/1991 | Blanchard | 5/424 |
| 5,040,253 A | 8/1991 | Cheng | 5/616 |
| 5,044,025 A | 9/1991 | Hunsinger et al. | 5/424 |
| 5,060,327 A | 10/1991 | Celestina et al. | 5/662 |
| 5,065,464 A | 11/1991 | Blanchard et al. | 5/81.1 R |

| | | | |
|---|---|---|---|
| 5,068,933 A | 12/1991 | Sexton | 5/644 |
| 5,072,463 A | 12/1991 | Willis | 5/618 |
| 5,077,843 A | 1/1992 | Dale et al. | 5/600 |
| 5,083,332 A | 1/1992 | Foster et al. | 5/185 |
| 5,083,334 A | 1/1992 | Huck et al. | 5/430 |
| 5,084,925 A | 2/1992 | Cook | 5/425 |
| 5,097,550 A | 3/1992 | Marra, Jr. | 5/424 |
| 5,121,512 A | 6/1992 | Kaufmann | 5/713 |
| 5,121,756 A | 6/1992 | Koledin | 5/628 |
| 5,129,117 A | 7/1992 | Celestina et al. | 5/602 |
| 5,168,589 A | 12/1992 | Stroh et al. | 5/710 |
| 5,175,897 A | 1/1993 | Marra, Jr. | 5/425 |
| 5,179,744 A | 1/1993 | Foster et al. | 5/600 |
| 5,187,824 A | 2/1993 | Stryker | 5/430 |
| 5,191,663 A | 3/1993 | Holder et al. | 5/424 |
| 5,193,633 A | 3/1993 | Ezenwa | 180/65.1 |
| 5,197,156 A | 3/1993 | Stryker et al. | 5/428 |
| D336,577 S | 6/1993 | Celestina et al. | D6/503 |
| 5,216,768 A | 6/1993 | Bodine et al. | 5/711 |
| 5,222,132 A | 6/1993 | Rioux, Jr. | 379/455 |
| 5,230,113 A | 7/1993 | Foster et al. | 5/608 |
| 5,235,258 A | 8/1993 | Schuerch | 318/16 |
| 5,239,300 A | 8/1993 | Berger | 341/176 |
| 5,246,272 A * | 9/1993 | Kato et al. | 297/364 |
| 5,255,403 A | 10/1993 | Ortiz | 5/503.1 |
| 5,265,450 A * | 11/1993 | Doyle | 70/118 |
| 5,279,010 A | 1/1994 | Ferrand et al. | 5/600 |
| 5,317,769 A | 6/1994 | Weismiller et al. | 5/610 |
| 5,325,551 A | 7/1994 | Tappel et al. | 5/709 |
| 5,365,623 A | 11/1994 | Springer | 5/658 |
| 5,370,111 A | 12/1994 | Reeder et al. | 128/202.13 |
| 5,377,370 A | 1/1995 | Foster et al. | 5/620 |
| 5,381,571 A | 1/1995 | Gabhart | 5/430 |
| 5,384,927 A | 1/1995 | Mardero et al. | 5/662 |
| 5,394,580 A | 3/1995 | Foster et al. | 5/620 |
| 5,408,710 A | 4/1995 | Garman et al. | 5/83.1 |
| 5,410,765 A | 5/1995 | Youngblood | 5/93.1 |
| 5,418,988 A | 5/1995 | Iura | 5/430 |
| 5,421,046 A | 6/1995 | Vande Streek | 5/624 |
| 5,450,641 A | 9/1995 | Montgomery | 5/663 |
| 5,454,126 A | 10/1995 | Foster et al. | 5/618 |
| 5,455,973 A | 10/1995 | Brumfield et al. | 5/424 |
| 5,479,666 A | 1/1996 | Foster et al. | 5/624 |
| 5,481,772 A | 1/1996 | Glynn et al. | 5/663 |
| 5,483,709 A | 1/1996 | Foster et al. | 5/81.1 R |
| 5,485,699 A | 1/1996 | Gabhart | 49/394 |
| 5,511,257 A * | 4/1996 | Hannes | 5/100 |
| 5,522,100 A | 6/1996 | Schilling et al. | 5/86.1 |
| 5,524,306 A | 6/1996 | George | 5/424 |
| 5,537,701 A | 7/1996 | Elliot | 5/617 |
| 5,542,135 A | 8/1996 | Ozrovitz et al. | 5/424 |
| 5,542,136 A | 8/1996 | Tappel | 5/710 |
| 5,542,138 A | 8/1996 | Williams et al. | 5/658 |
| 5,557,817 A | 9/1996 | Haddock | 5/663 |
| 5,564,784 A | 10/1996 | Felling | 297/344.23 |
| 5,575,025 A | 11/1996 | Peters | 5/600 |
| 5,577,277 A | 11/1996 | Sundberg et al. | 5/426 |
| 5,577,279 A | 11/1996 | Foster et al. | 5/618 |
| 5,577,452 A * | 11/1996 | Yindra | 108/168 |
| 5,586,346 A | 12/1996 | Stacy et al. | 5/710 |
| 5,611,096 A | 3/1997 | Bartlett et al. | 5/617 |
| 5,625,913 A * | 5/1997 | Singleton | 5/609 |
| 5,642,545 A | 7/1997 | Howard | 5/663 |
| 5,671,490 A | 9/1997 | Wu | 5/426 |
| 5,678,267 A | 10/1997 | Kinder | 5/662 |
| 5,689,839 A | 11/1997 | Laganiere et al. | 5/425 |
| 5,715,548 A | 2/1998 | Weismiller et al. | 5/624 |
| 5,732,423 A | 3/1998 | Weismiller et al. | 5/425 |
| 5,737,781 A | 4/1998 | Votel | 5/81.1 HS |
| 5,745,937 A | 5/1998 | Weismiller et al. | 5/624 |
| 5,745,939 A | 5/1998 | Flick et al. | 5/648 |
| 5,749,112 A | 5/1998 | Metzler | 5/663 |
| 5,761,756 A | 6/1998 | Nowak et al. | 5/426 |
| 5,771,506 A | 6/1998 | Joiner | 4/575.1 |
| 5,781,945 A | 7/1998 | Scherer et al. | 5/426 |
| 5,802,636 A | 9/1998 | Corbin et al. | 5/425 |
| 5,802,640 A | 9/1998 | Ferrand et al. | 5/617 |
| 5,832,549 A | 11/1998 | Le Pallec et al. | 5/430 |
| 5,864,900 A | 2/1999 | Landau | 5/427 |
| 5,878,452 A | 3/1999 | Brooke et al. | 5/428 |
| 5,926,873 A | 7/1999 | Fountain | 5/424 |
| 5,946,953 A * | 9/1999 | Feldpausch | 70/78 |
| 5,975,592 A * | 11/1999 | Lin | 292/37 |
| 5,987,666 A | 11/1999 | Zigmont | 5/424 |
| 6,008,598 A | 12/1999 | Luff et al. | 318/16 |
| 6,021,533 A | 2/2000 | Ellis et al. | 5/600 |
| 6,038,721 A | 3/2000 | Gordon | 5/663 |
| 6,058,531 A | 5/2000 | Carroll | 5/430 |
| 6,089,593 A | 7/2000 | Hanson et al. | 280/650 |
| 6,182,310 B1 | 2/2001 | Weismiller et al. | 5/425 |
| 6,240,580 B1 | 6/2001 | Hamilton et al. | 5/425 |
| 6,253,397 B1 | 7/2001 | Bartow et al. | 5/430 |
| 6,336,235 B1 | 1/2002 | Ruehl | 5/610 |
| 6,347,422 B1 | 2/2002 | Heavrin | 5/663 |
| 6,360,385 B1 | 3/2002 | Lewandowski | 5/430 |
| 6,363,552 B1 | 4/2002 | Hornbach et al. | 5/425 |
| 6,374,440 B1 | 4/2002 | Thim, Jr. | 5/633 |
| 6,401,277 B1 | 6/2002 | Savage et al. | 5/430 |
| 6,427,264 B1 | 8/2002 | Metz et al. | 5/425 |
| 6,446,283 B1 * | 9/2002 | Heimbrock et al. | 5/425 |
| 6,615,426 B1 | 9/2003 | Risk, Jr. | 5/425 |
| 6,622,364 B1 | 9/2003 | Hamilton et al. | 29/416 |
| 6,611,979 B1 | 11/2003 | Welling et al. | 5/624 |
| 6,640,360 B1 | 11/2003 | Hornbach et al. | 5/425 |
| 6,640,361 B1 * | 11/2003 | Heimbrock et al. | 5/430 |
| 6,662,391 B1 | 12/2003 | Wilson et al. | 5/600 |
| 6,668,399 B1 | 12/2003 | Malstaff et al. | 5/424 |
| 6,691,346 B1 | 2/2004 | Osborne et al. | 5/600 |
| 6,751,815 B1 * | 6/2004 | Heimbrock et al. | 5/53.1 |
| 2003/0019035 A1 * | 1/2003 | Heimbrock et al. | 5/428 |
| 2004/0025253 A1 * | 2/2004 | Heimbrock et al. | 5/425 |
| 2004/0177443 A1 * | 9/2004 | Simmonds et al. | 5/428 |

FOREIGN PATENT DOCUMENTS

| | | |
|---|---|---|
| EP | 1108410 A2 | 6/2001 |
| FR | 999408 | 1/1952 |
| GB | 2 199 803 | 7/1988 |
| WO | WO 9304253 A1 * | 3/1993 |
| WO | WO 98/17153 | 4/1998 |
| WO | WO 00/07537 | 2/2000 |
| WO | WO 00/69386 | 11/2000 |
| WO | WO 01/47340 | 7/2001 |
| WO | WO 01/62151 | 8/2001 |

OTHER PUBLICATIONS

A Hill-Rom Solution, "Med-Surg Bed Accessories" 1997.

* cited by examiner

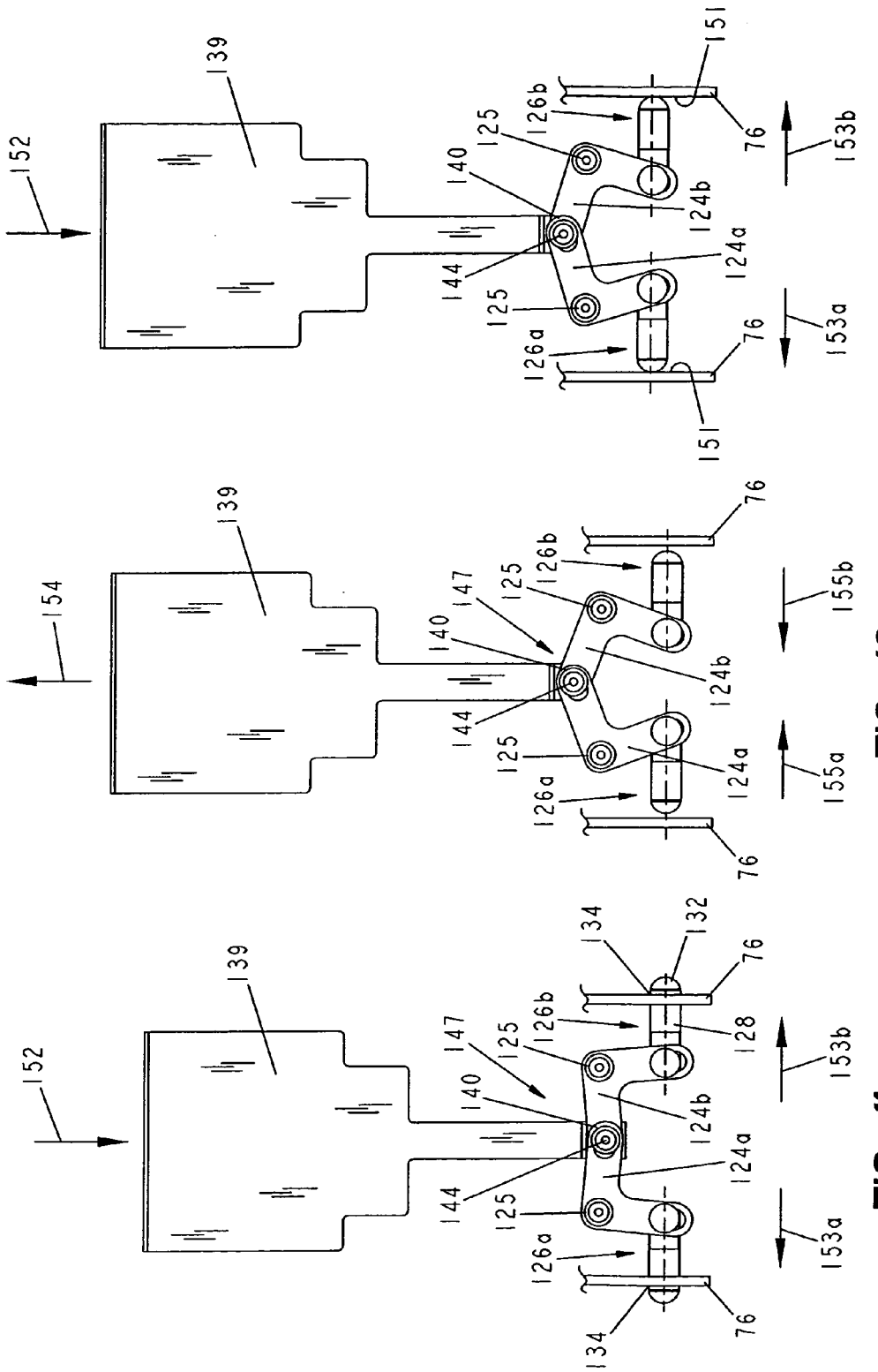

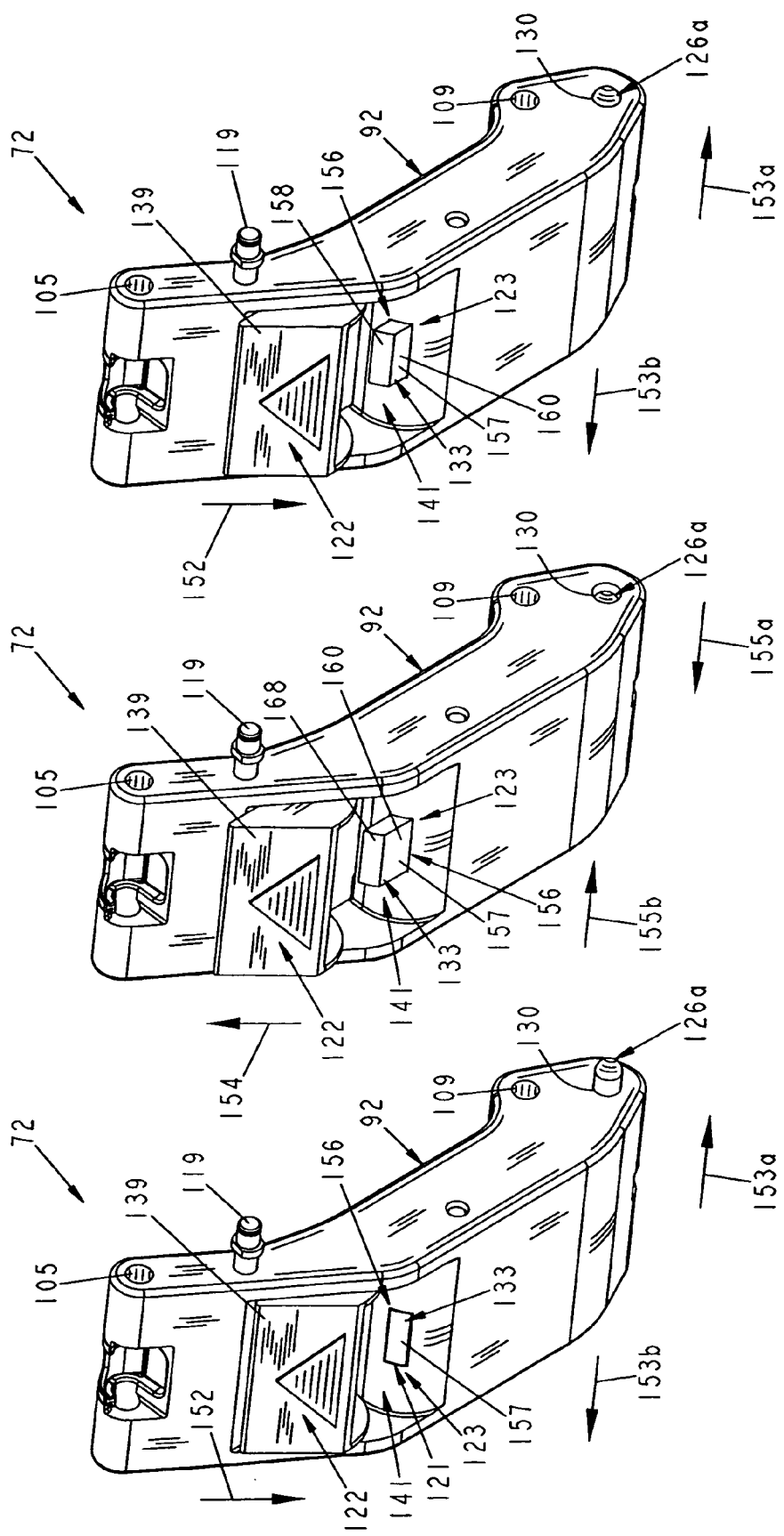

BED SIDERAIL HAVING A LATCH

CROSS-REFERENCE TO RELATED APPLICATIONS

This application is a continuation-in-part of U.S. patent application Ser. No. 10/657,696, filed Sep. 8, 2003, which claims the benefit of U.S. Provisional Patent Application Ser. No. 60/408,698, filed Sep. 6, 2002; U.S. Provisional Patent Application Ser. No. 60/409,748, filed Sep. 11, 2002; U.S. Provisional Patent Application Ser. No. 60/489,171, filed Jul. 22, 2003; and U.S. Provisional Patent Application Ser. No. 60/490,467, filed Jul. 28, 2003. This application further claims the benefit of U.S. Provisional Patent Application Ser. No. 60/458,720, filed Mar. 28, 2003. The disclosures of the above-identified patent applications are all expressly incorporated herein by reference.

BACKGROUND AND SUMMARY OF THE INVENTION

The present invention relates to a hospital bed. More particularly, the present invention relates to a hospital bed including a patient support surface and siderails movable relative to the patient support surface.

Hospital bed and other patient supports are known. Typically, such patient supports are used to provide a support surface for patients or other individuals for treatment, recuperation, or rest. Many such patient supports include a frame, a deck supported by the frame, a mattress, siderails configured to block egress of a patient from the mattress, and a controller configured to control one or more features of the bed.

In an illustrative embodiment of the invention, a patient support includes a frame, a mattress supported by the frame, and a siderail supported by the frame. The siderail includes a rail member, a linkage configured to permit vertical movement of the rail member between a raised position and a lowered position, and a latching mechanism configured to retain the rail member in at least one of the raised position and the lowered position.

Illustratively, the latching mechanism includes a rocker arm having first and second ends movable about a pivot axis, a handle member coupled proximate the first end of the rocker arm, and a latch member coupled proximate the second end of the rocker arm. The handle member is configured to pivot the rocker arm about the pivot axis such that the rocker arm moves the latch member between a latched position which prevents vertical movement of the rail member and an unlatched position which permits vertical movement of the rail member.

In an further illustrative embodiment, a patient support includes a frame, a mattress supported by the frame, and a siderail supported by the frame. The siderail includes a rail member and a linkage configured to permit vertical movement of the rail member, and a latch member configured to move between a latched position and an unlatched position. The latch member in the unlatched position permits vertical movement of the rail member and the latch member in the latch position retains the rail member in a vertical position. A latch position indicator is operably coupled to the latch member and is configured to provide an indication of the latch member being in the unlatched position.

In another illustrative embodiment, a patient support includes a frame, a mattress supported by the frame, and a siderail supported by the frame. The siderail includes a rail member, a linkage configured to permit vertical movement of the rail member, and a latch member having a latched position and an unlatched position, the latch member in the latched position being configured to prevent vertical movement of the rail member. The patient support further includes means for providing an indication that the latch member is in at least one of the latched and the unlatched positions.

In yet another illustrative embodiment, a method of indicating an unlatched position of a siderail is provided. The method comprises the steps of providing a frame, providing a mattress supported by the frame, and providing a siderail supported by the frame. The siderail includes a rail member, a linkage configured to permit vertical movement of the rail member between a raised position and a lowered position, and a latch member including a latched position and an unlatched position, the latch member in the latched position being configured to prevent vertical movement of the rail member. The method further comprises the steps of lifting the rail member to the raised position, and providing a visual indication of whether the latch is in the latched position.

In a further illustrative embodiment, a patient support includes a frame, a patient support surface supported by the frame, a first component coupled to the frame, and a second component operably coupled to the first component and configured to move relative to the first component between a first position and a second position. A position indicator is coupled to the second component and is movable between a first position and a second position, the position indicator including a body having an indicating surface. The housing is configured to receive the position indicator, wherein the indicating surface of the position indicator is not visible from outside the housing when the position indicator is in the first position and the indication surface of the position indicator is visible outside the housing when the position indicator is in the second position.

Additional features and advantages of the present invention will become apparent to those skilled in the art upon consideration of the following detailed description of the presently perceived best mode of carrying out the invention.

BRIEF DESCRIPTION OF THE DRAWINGS

The detailed description particularly refers to the accompanying figures in which:

FIG. 11 is a side elevational view of the latch in a fully latched position;

FIG. 12 is a view similar to FIG. 11, showing the latch in an unlatched position;

FIG. 13 is a view similar to FIGS. 11 and 12, showing the latch in a false latched position, intermediate the fully latched position of FIG. 11 and the unlatched position of FIG. 12;

FIG. 14 is a perspective view of the link of FIG. 10, showing pins of the latch extending out from the link when the latch is in the fully latched position of FIG. 10;

FIG. 15 is a view similar to FIG. 14, showing the pins withdrawn into the link when the latch is in the unlatched position of FIG. 12;

FIG. 16 is a view similar to FIGS. 14 and 15, showing the pins at least partially withdrawn into the link when the latch is in the false latched position of FIG. 13;

DETAILED DESCRIPTION OF THE DRAWINGS

Figure 1:
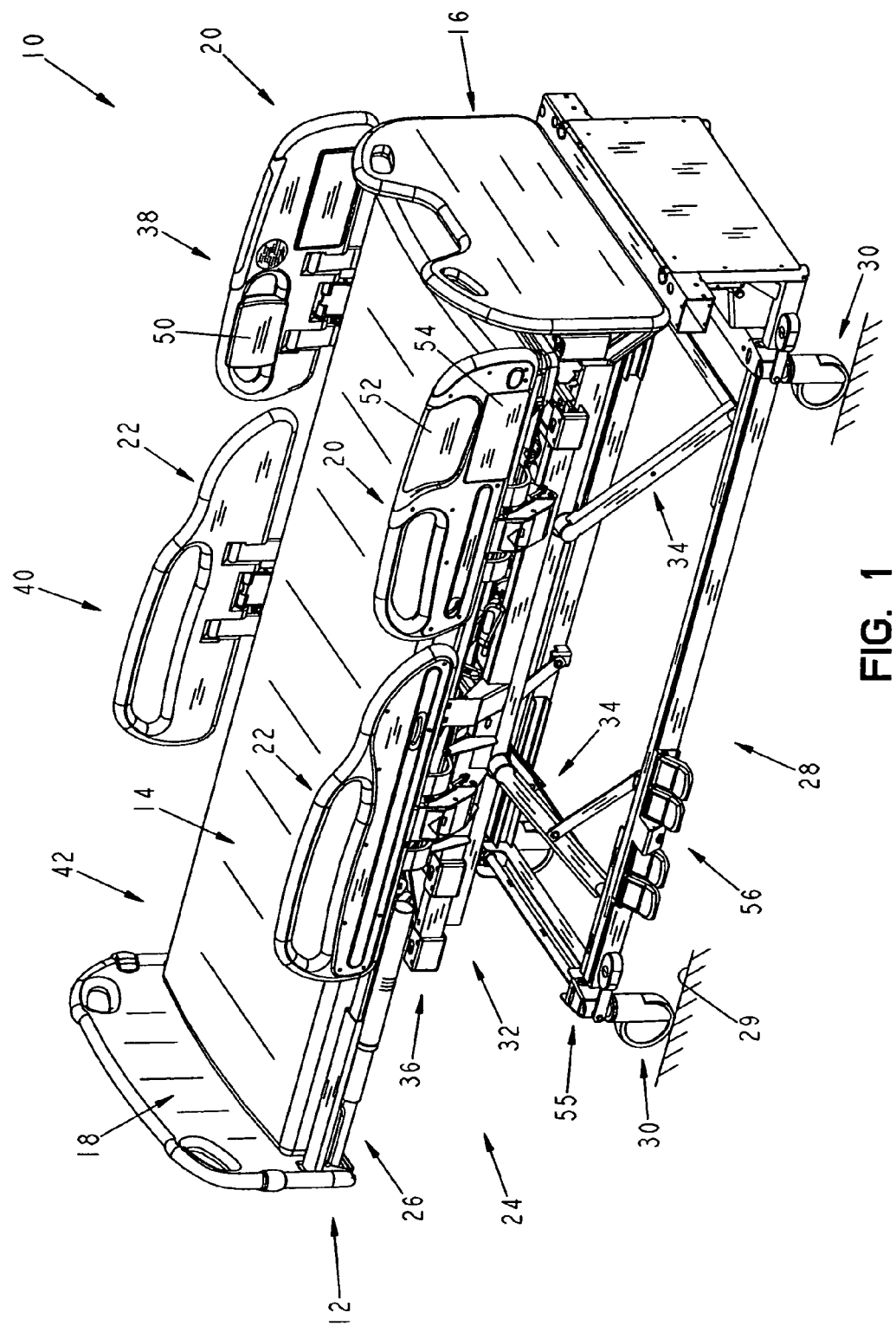
FIG. 1 is a perspective view of a patient support showing the patient support including a deck support, a deck having a plurality of sections coupled to and positioned above the deck support, a mattress supported by the deck, a headboard coupled to the deck support, a first pair of head end siderails coupled to the deck and a second pair of foot end siderails coupled to the deck support.
Figure 2:
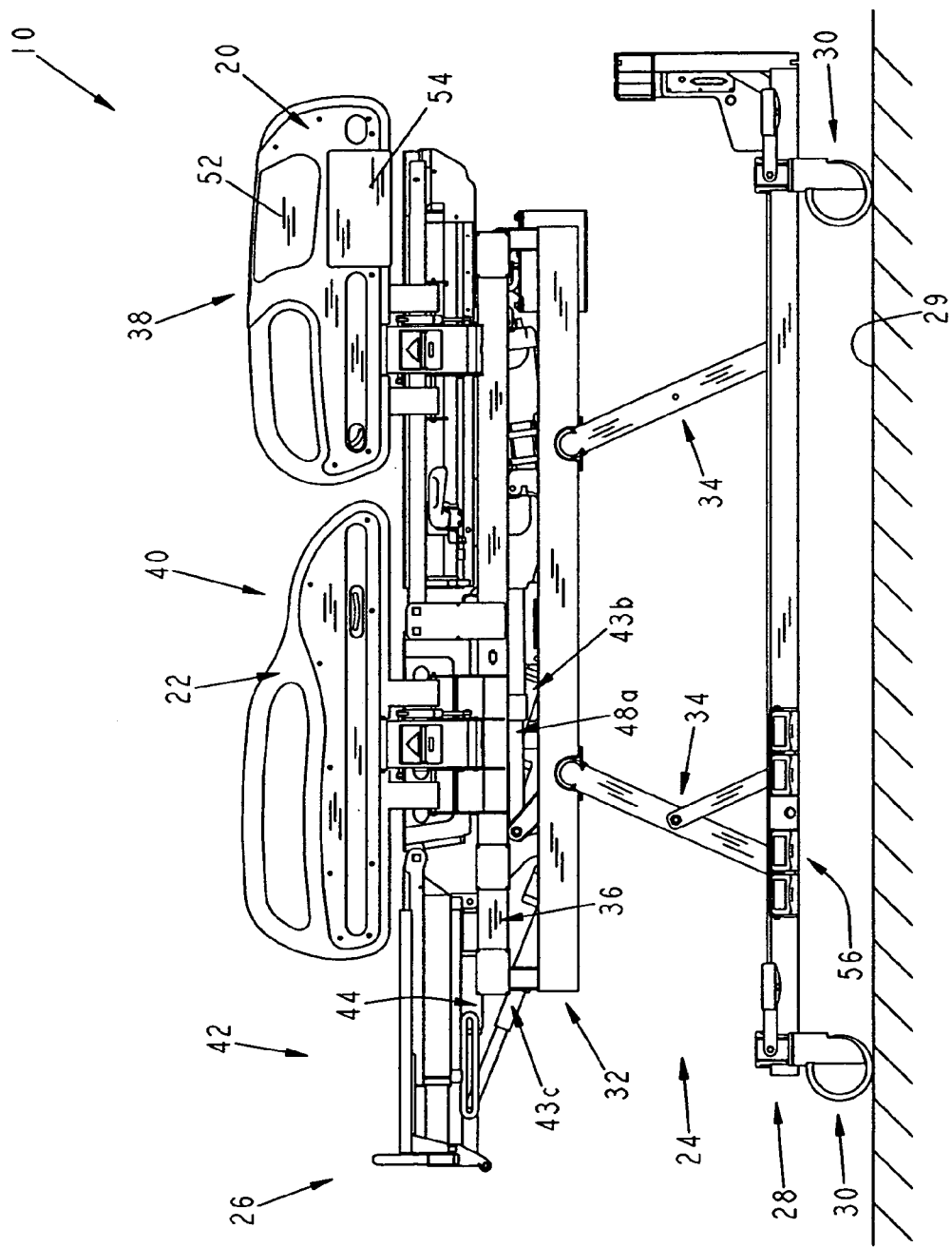
FIG. 2 is a side elevation view of the patient support of FIG. 1, showing the deck support in an upper position and the deck sections in a linear relationship or bed configuration.
Figure 3:
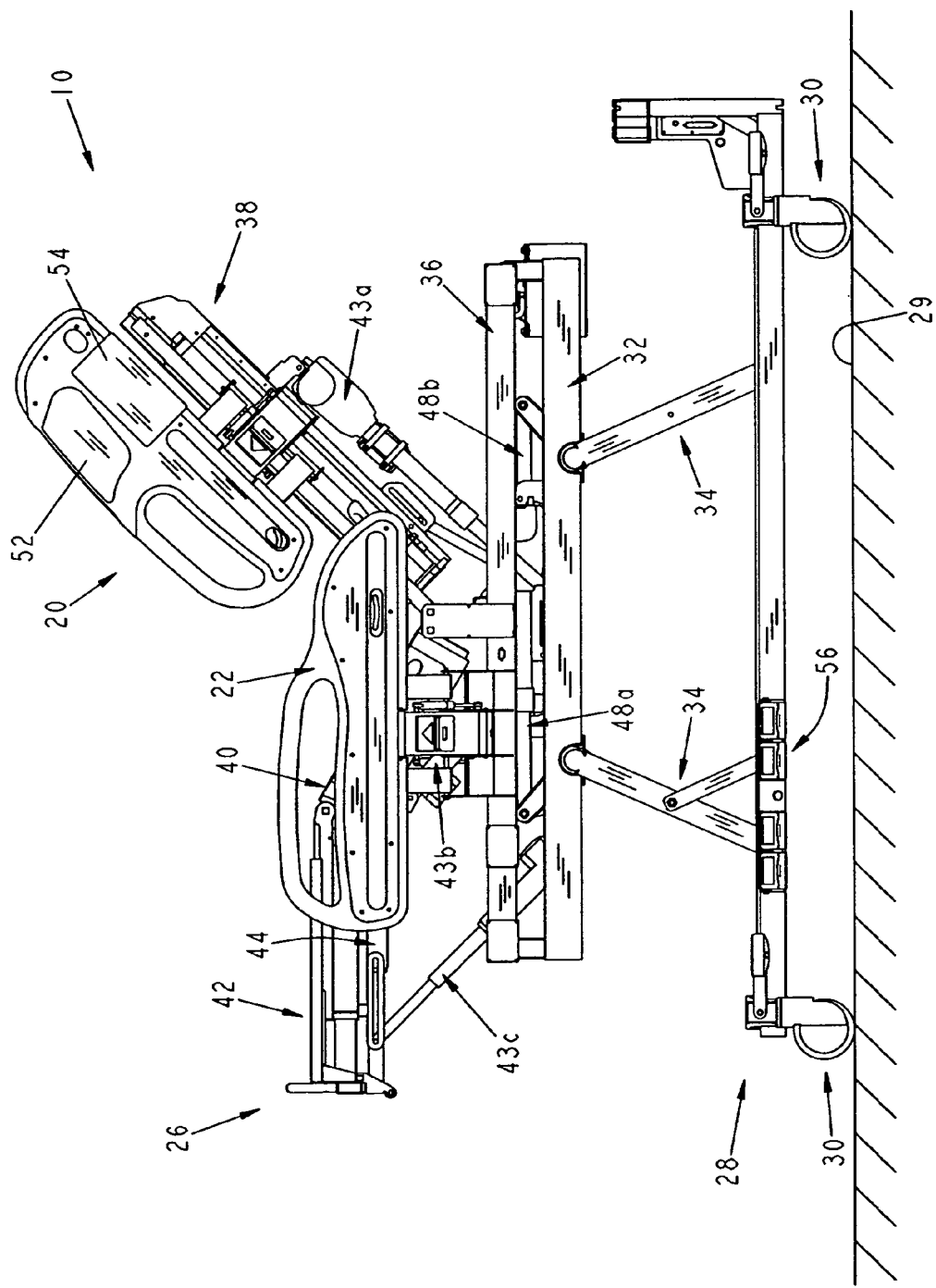
FIG. 3 is a side elevation view of the patient support of FIG. 1, showing the deck support in the upper position of FIG. 2 and a head section of the deck elevated by a head section actuator and a seat section of the deck elevated by a seat section actuator.

A patient support 10 according to an illustrative embodiment of the present invention is shown in FIGS. 1–3. Patient support 10 includes a frame 12, a mattress 14 supported by frame 12, a headboard 16, a footboard 18, a pair of head end siderails 20, and a pair of foot end siderails 22. Frame 12 includes a deck support 24 and a deck 26 supporting mattress 14. Deck support 24 includes a base frame 28 supported on the floor 29 by a plurality of caster wheels 30, an intermediate frame 32, first and second pairs of lift arms 34 configured to raise and lower intermediate frame 32 relative to base frame 28, and a weigh frame 36 supported by intermediate frame 32.

Deck 26 is supported by weigh frame 36 and is configured to articulate between a plurality of positions. More particularly, deck 26 illustratively includes a head section 38 pivotably coupled to weigh frame 32, a seat section 40 pivotably coupled to weigh frame 32, and an adjustable length leg section 42 pivotably coupled to seat section 40. The deck 26 is illustrated in a first configuration in FIGS. 1 and 2, while the deck 26 is illustrated in a second configuration in FIG. 3. In the first configuration of FIGS. 1 and 2, head section 38, seat section 40, and leg section 42 are in a substantially linear or planar relationship. In the second configuration of FIG. 3, head section 38 of deck 26 is elevated by a head section actuator 43a and seat section 40 of deck 26 is elevated by a seat section actuator 43b. A leg section actuator 43c is likewise configured to move leg section 42 relative to seat section 40. An extension actuator 44 is configured to extend and retract the adjustable length leg section 42.

Additional details of illustrative deck support 24 and deck 26 may be found in U.S. Pat. No. 6,658,680, issued Dec. 9, 2003 and U.S. Pat. No. 6,611,979, issued Sep. 2, 2003, both of which are assigned to the assignee of the present invention and the disclosures of which are expressly incorporated herein by reference.

Head end siderails 20 are coupled to head section 38 of deck 26 and may be moved relative to mattress 14 between raised and lowered positions. Foot end siderails 22 are coupled to weigh frame 32 and may also be moved relative to mattress 14 between raised and lowered positions.

Figure 4:
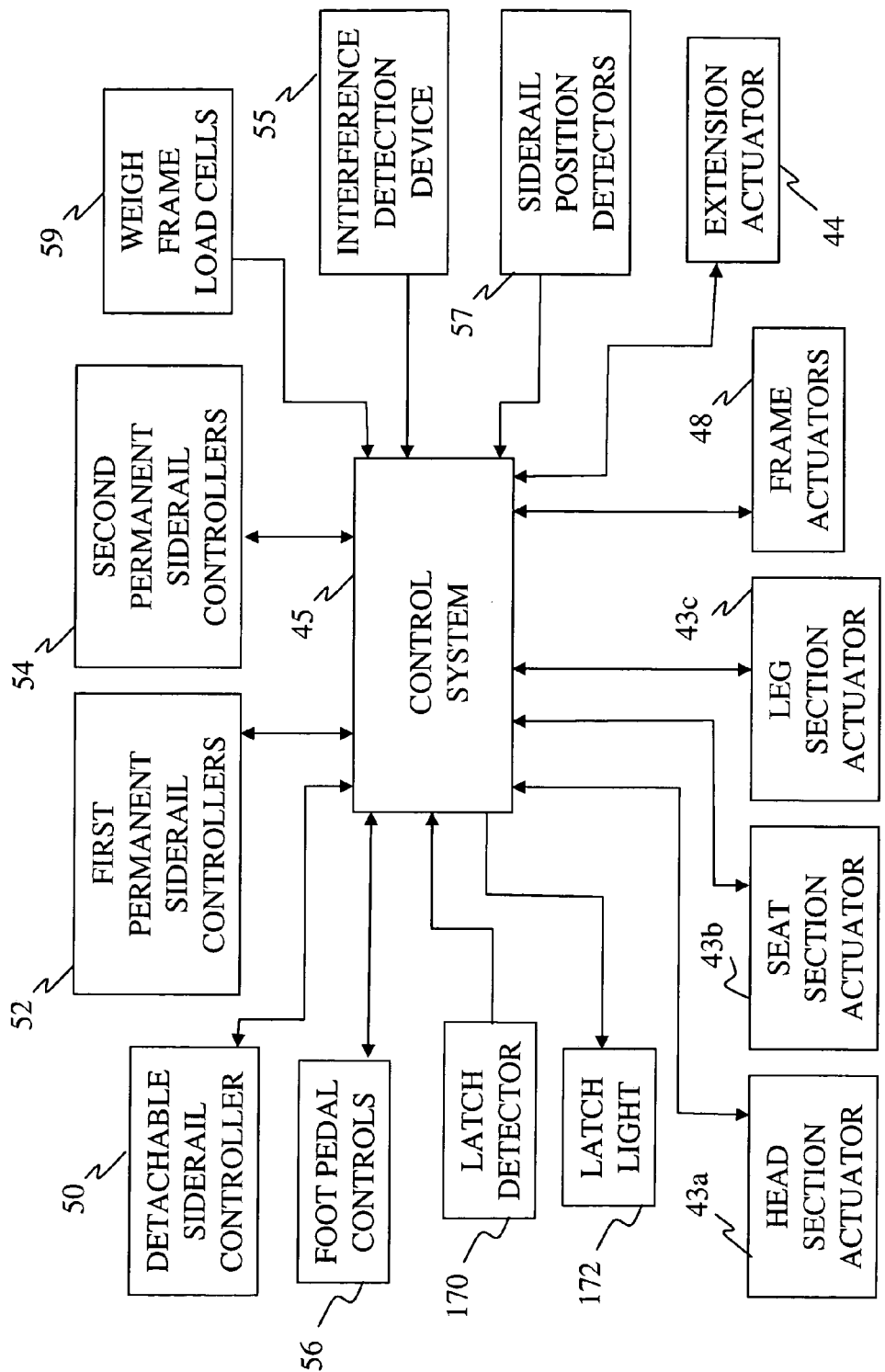
FIG. 4 is a block diagram illustrating communication between the control system and various components of the patient support.

Referring now to FIG. 4, a control system 45 provides control of various functions of patient support 10. Control system 45 operates and monitors linear actuator 44 to extend and retract adjustable length leg section 42, and linear actuators 48 to move intermediate frame 32 relative to base frame 28. Control system 45 further operates and monitors linear actuators 43a, 43b and 43c to move head section 38 relative to weigh frame 36, seat section 40 relative to weigh frame 36, and leg section 42 relative to seat section 40, respectively.

Control system 45 includes a plurality of input devices including a detachable siderail controller 50 configured to removably couple to any of head and foot end siderails 20, 22, a first pair of permanent siderail controllers 52 coupled to head end siderails 20, a second pair of permanent siderail controllers 54 pivotably coupled to head end siderails 20, and a pair of foot pedal controls 56 coupled to base frame 28. An illustrative foot pedal control is disclosed in U.S. Pat. No. 6,691,346, issued Feb. 17, 2004, which is assigned to the assignee of the present invention and the disclosure of which is expressly incorporated herein by reference.

Control system 45 also illustratively includes an interference detection device 55 coupled to base frame 28 to detect possible clearance issues between intermediate frame 32 and base frame 28. Control system 45 further illustratively includes a plurality of actuator position detectors or motor sensors (not shown) provided with each of the plurality of actuators 43a, 43b, 43c, 44, 48. A plurality of load cells 59 are provided between weigh frame 36 and intermediate frame 32 to provide signals that indicate the weight supported by intermediate frame 32. Control system 45 uses these signals to determine the weight of a patient positioned on mattress 14. Additionally, control system 45 illustratively includes a plurality of siderail position detectors or sensor 57 configured to provide signals indicative of the vertical position of siderails 20, 22.

As previously described and as shown in FIG. 1, deck support 24 includes a base frame 28 supported on the floor 29 by a plurality of caster wheels or caster devices 30, an intermediate frame 32, first and second pairs of lift arms 34 configured to raise and lower intermediate frame 32 relative to base frame 28, and a weigh frame 36 supported by intermediate frame 32. Linear actuators 48a and 48b, shown in FIG. 3, provide power to actuate lift arms 34 and in turn to raise and lower intermediate frame 32 relative to base frame 28.

Figure 5:
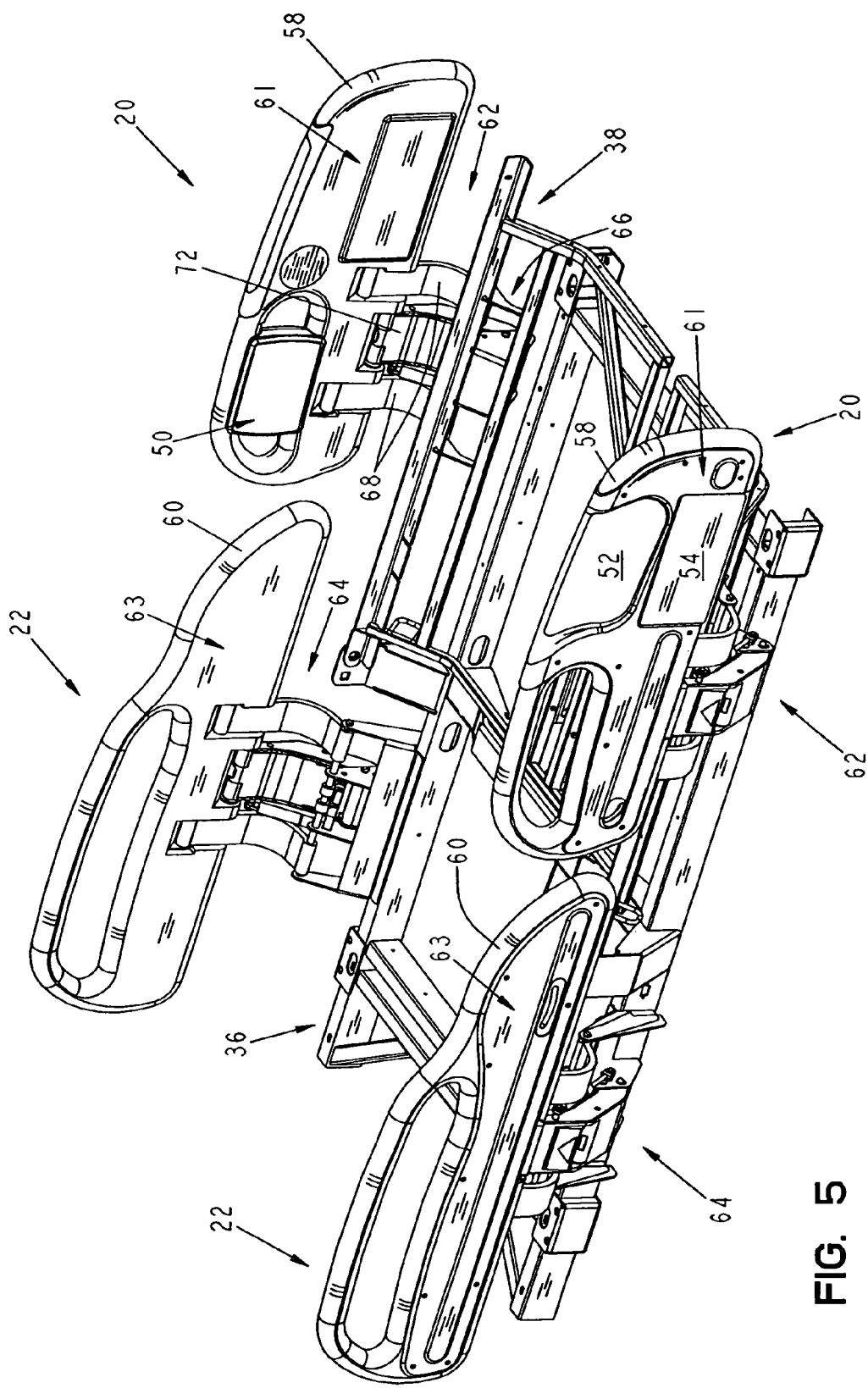
FIG. 5 is a perspective view of the weigh frame and portions of the deck, showing the head end and foot end siderails in raised positions.
Figure 6:
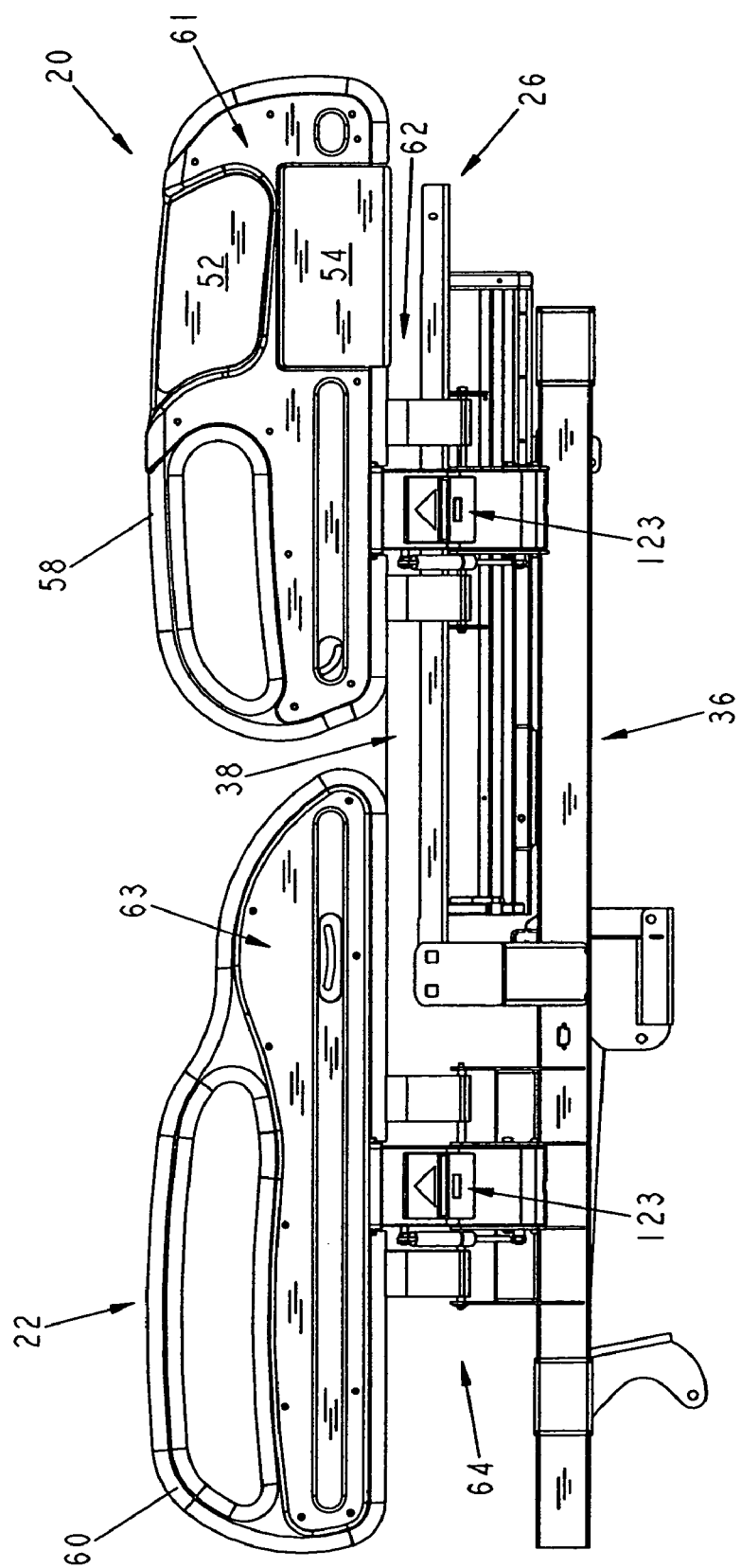
FIG. 6 is a side elevation view of the weigh frame and portions of the deck, showing the head end and foot end siderails in the raised positions.
Figure 7:
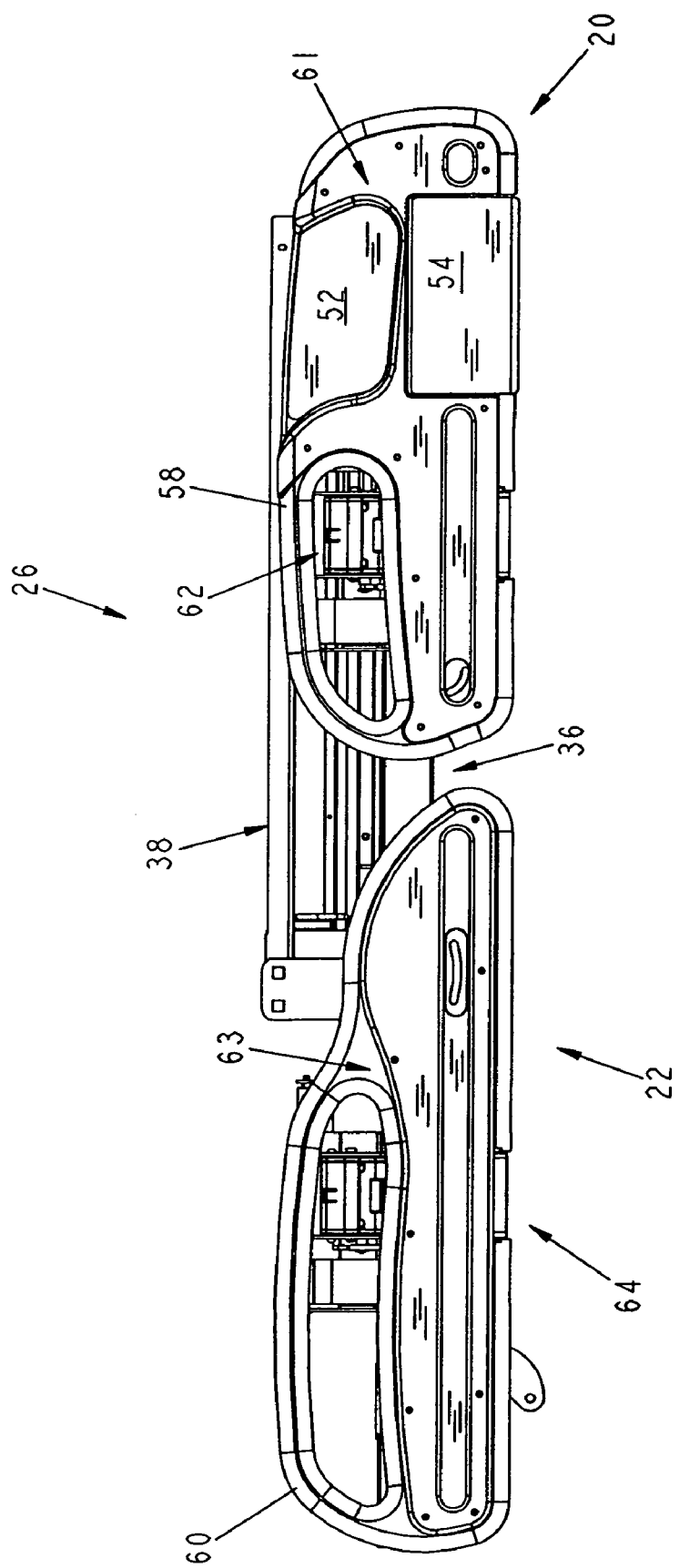
FIG. 7 is a view similar to FIG. 6, showing the head end and foot end siderails in lowered positions.

Head and foot end siderails 20, 22 are configured to move between upper positions, as shown in FIGS. 5 and 6, and lower positions, as shown in FIG. 7, to permit entry and egress of patients into and out of patient support 10. Siderails 20 are coupled to head section 38 of deck 26 and siderails 22 are coupled to weigh frame 36. Thus, as head section 38 of deck 26 rotates relative to weigh frame 36, head end siderails 20 also rotate relative to weigh frame 36. However, regardless of the movement of sections 38, 40, 42, foot end siderails 22 do not move relative to weigh frame 36.

Siderails 20 include rail members 58 and linkage assemblies 62 coupled between rail members 58 and head section 38. Likewise, siderails 22 include rail members 60 and linkage assemblies 64 coupled between rail members 60 and weigh frame 36. Linkage assemblies 62, 64 permit rail members 58, 60 each to be moved between the upper position, as shown in FIGS. 5 and 6, and the lower position, as shown in FIG. 7. Rail members 58, 60 each include a body 61, 63, respectively, defining a barrier when in a raised position. Body 61, 63 may include a thermoplastic material supported by a rigid internal frame.

Figure 8:
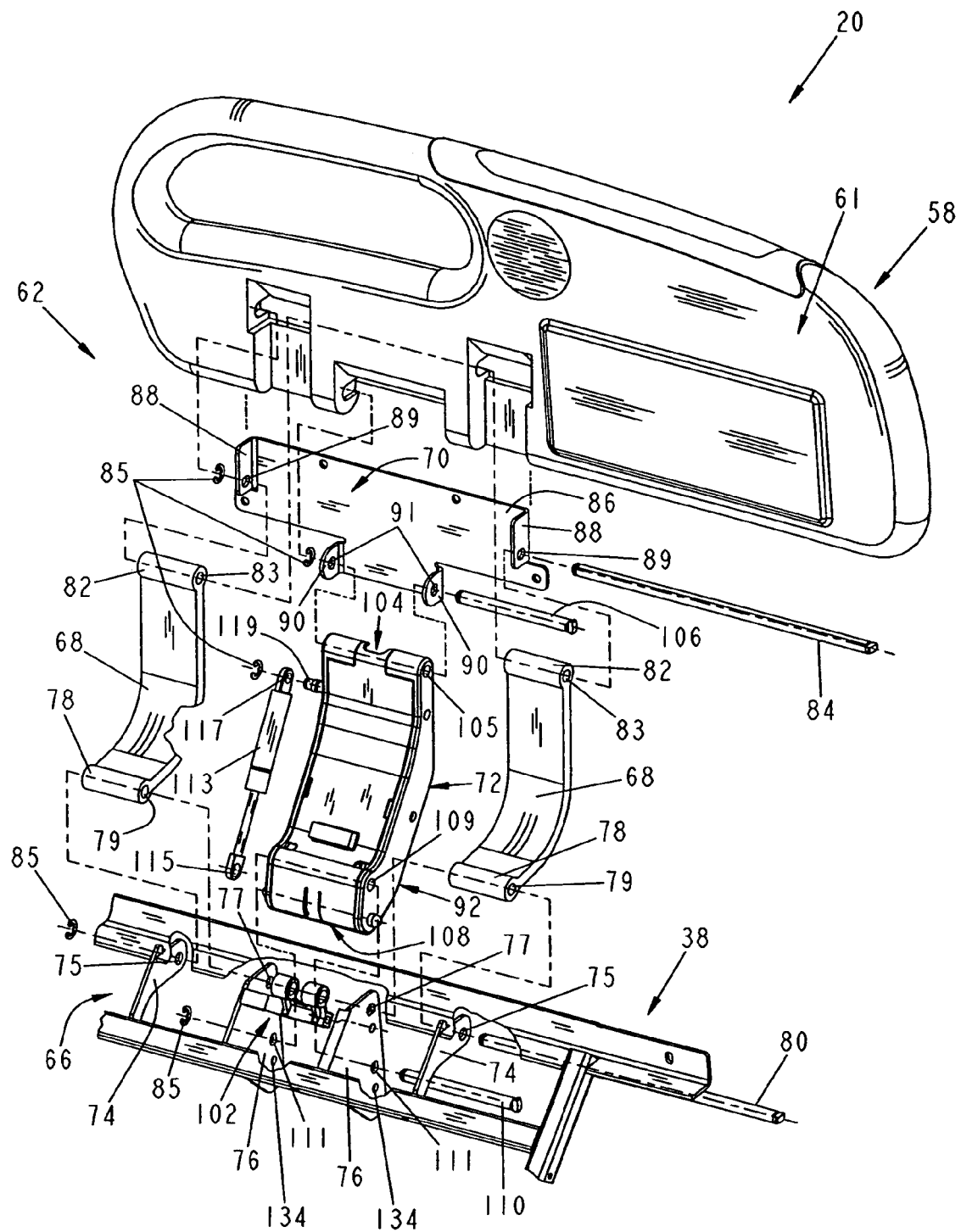
FIG. 8 is an exploded perspective view of the head end siderail.

With reference to FIG. 8, linkage assembly 62 of head end siderail 20 includes a first link 66 rigidly coupled to head section 38, a pair of curved second links 68 pivotably coupled to first link 66, a third link 70 pivotably coupled to second links 68, and a curved fourth link 72 pivotably coupled to third and first links 70 and 66. First link 66 includes a first pair of flanges 74 welded to head section 38, and a second pair of flanges 76 welded to head section 38. The second pair of flanges 76 are positioned intermediate the first pair of flanges 74. Each second link 68 includes a looped first end 78 pivotably coupled to flanges 74 and 76 of first link 66 by a rod 80, and a looped second end 82 pivotably coupled to third link 70 by a rod 84. More particularly, rod 80 is received within coaxially aligned apertures 75, 77, and 79 formed within the flanges 74 and 76 and the looped first ends 78 of second link 68, respectively. Axial movement of rods 80 and 84 is prevented by C-shaped or open retaining rings 85 of the type known in the art.

Third link 70 includes a base plate 86, a first pair of inwardly extending flanges 88 coupled to base plate 86, and a second pair of inwardly extending flanges 90 also coupled to base plate 86 as shown in FIG. 8. The base plate 86 is coupled to the body 61 of the rail member 58. Rod 84 extends between flanges 88 and through second ends 82 of second link 68 to provide the pivotable connection therebetween. More particularly, rod 84 is received within coaxially aligned apertures 89 and 83 formed within flanges 88 and looped second ends 82 of second link 68, respectively.

Figure 10:
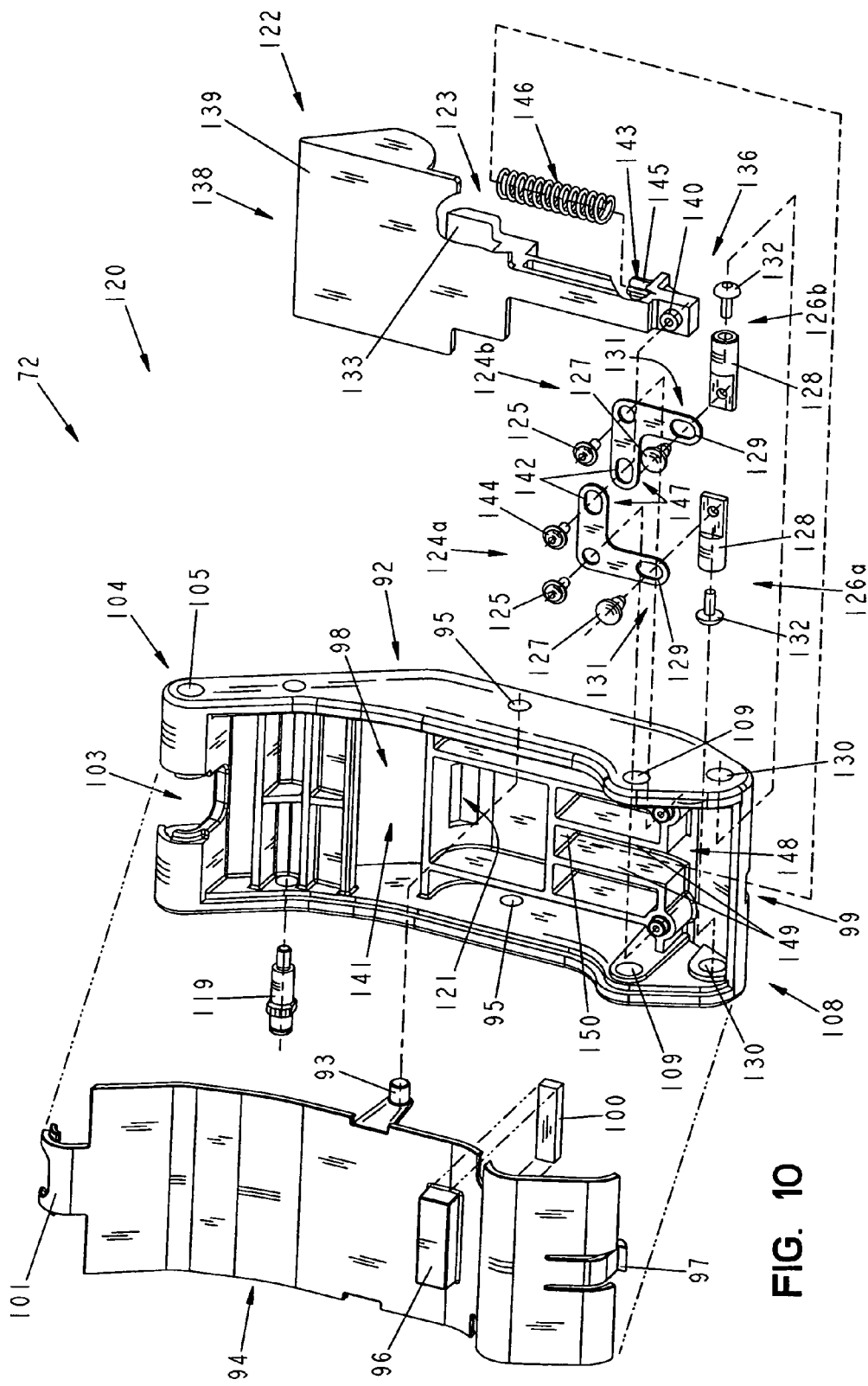
FIG. 10 is an exploded perspective view of a link of the head end siderail and a latch coupled to the link.

As shown in FIGS. 8 and 10, fourth link 72 includes a base 92 and a cover 94, which together define a latch-receiving void 98. The cover 94 is illustratively removably secured to the base 92 by a pair of resilient side tabs or pegs 93 which are receivable within a pair of respective apertures 95 formed in the base 92. Similarly, a resilient lower tab 97 is receivable within a slot 99 formed in the base 92, and an upper tab 101 is receivable within a notch 103 formed in the base 92. A first end 104 of base 92 is pivotably coupled to second pair of flanges 90 of third link 70 by a rod 106. Rod 106 is received within coaxially aligned apertures 91 and 105 formed within the flanges 90 and first end 104 of base 92, respectively. Similarly, a second end 108 of base 92 is pivotably coupled to the lower ends of flanges 76 of first link 66 by a rod 110. Rod 110 is received within coaxially aligned apertures 111 and 109 formed within the flanges 76 and the second end 108 of base 92, respectively. Axial movement of rods 106 and 110 is prevented by C-shaped or open retaining rings 85 of the type known in the art. Thus, linkage assembly 62 provides a four bar linkage permitting head end siderail 20 to swing between the upper position and the lower position.

A biasing device 113, illustratively a conventional gas spring, may extend intermediate first link 66 and fourth link 72 in order to assist in the raising and the lowering of siderail 20. A first end 115 of the biasing device 113 is pivotably coupled to rod 80, while a second end 117 of the biasing device 113 is pivotably coupled to a connector 119. Connector 119 is illustratively coupled proximate the first end 104 of base 92 of fourth link 72. Biasing device 113 illustratively provides an upwardly acting force to control the rate of descent of siderail 20 and to assist the caregiver 56 in raising siderail 20.

Cover 94 includes a pocket 96 configured to receive a rectangular magnet 100 therein. Magnet 100 is coupled to cover 94 and rotates with fourth link 72 during raising and lowering of head end siderail 20. A Hall effect sensor 102 is coupled to flanges 76 of first link 66 and to rod 80, and is configured to detect the position of magnet 100. Magnet 100 together with a Hall effect sensor 102 define an illustrative siderail position detector 57 for communication with control system 45 as shown in FIG. 4. Based on the position of magnet 100 relative to Hall effect sensor 102, control system 45 knows when head end siderail 20 is in the raised position and the lowered position.

Figure 9:
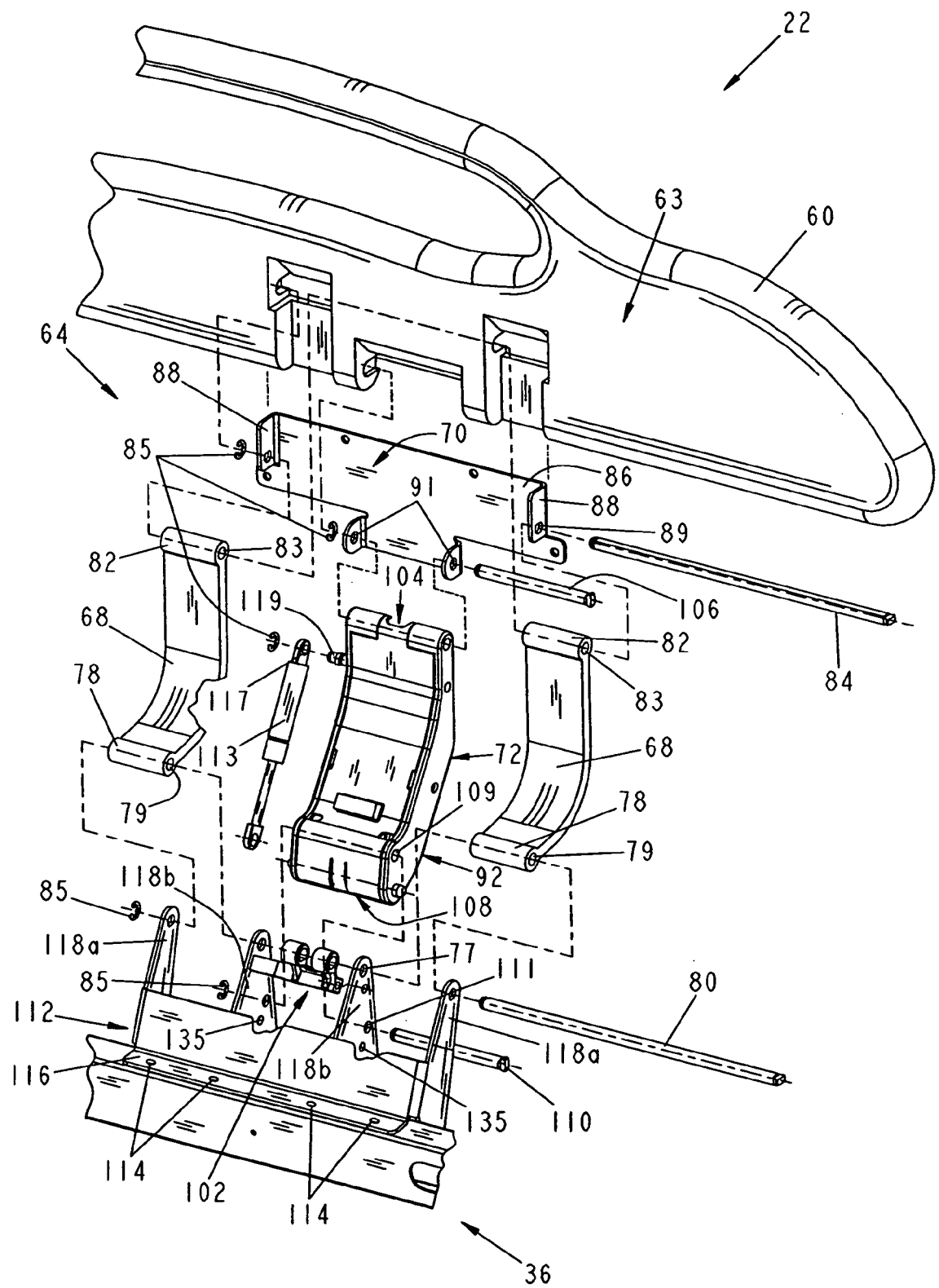
FIG. 9 is an exploded perspective view of the foot end siderail.

With reference to FIG. 9, linkage assembly 64 of foot end siderail 22 is substantially similar to linkage assembly 62 of head end siderail 20. As such, like components are identified with the same reference numbers as described above with respect to head end siderail 20. Linkage assembly 64 includes a first link 112 rigidly coupled to weigh frame 36, pair of curved second links 68 pivotably coupled to first link 112, third link 70 pivotably coupled to second links 68, and curved fourth link 72 pivotably coupled to third and first links 70, 112.

First link 112 includes a base 116 coupled to weigh frame 36 by fasteners 114 and having outer and inner pairs of upwardly extending flanges 118a, 118b rigidly coupled to base 116. Each second link 68 has its looped first end 78 pivotably coupled to flanges 118a, 118b of first link 112 by rod 80, and has its looped second end 82 pivotably coupled to flanges 88 of third link 70 by rod 84. First end 104 of base 92 of fourth link 72 is pivotably coupled to flanges 90 of third link 70 by rod 106. Second end 108 of base 92 is pivotably coupled to the lower ends of inner flanges 118b of first link 112 by rod 110. Base plate 86 of third link 70 is coupled to body 61 of rail member 60. Axial movement of rods 80, 84, 106, and 110 is prevented by C-shaped or open retaining rings 85 of the type known in the art. Thus, linkage assembly 64 provides a four bar linkage permitting foot end siderail 22 to swing between the upper and lower positions.

Each siderail 20, 22 further includes a latching mechanism or retainer 120 configured to "bind" the four bar linkage to prevent siderails 20, 22 from moving from the upper position to the lower position. As shown in FIG. 10, retainer 120 illustratively includes a slide or handle member 122 positioned in void 98 to slide relative to base 92 and cover 94 of fourth link 72. Illustratively, a latch position indicator 123 is operably coupled to retainer 120 and is configured to extend within an opening 121 formed in base 92. Retainer 120 is configured to move between a latched position, as shown in FIGS. 11 and 14, and an unlatched position, as shown in FIGS. 12 and 15. A false latched position, as detailed herein, is shown in FIGS. 13 and 16. A pair of L-shaped rocker arms or members 124a, 124b are pivotably coupled to base 92 by pivot pins, illustratively shoulder screws 125. A pair of latch members or pins 126a, 126b are pivotably coupled to respective rocker arms 124a, 124b by pivot pins, illustratively shoulder screws 127 received within slots 129 formed in a first end 131 of the respective rocker arm 124a, 124b. Latch pins 126 are configured to extend through apertures 130 in base 92 near second end 108, and into apertures 134, 135 in flanges 76, 118*b* of first links 66, 112, respectively. Pins 126 include body members 128 and head members 132 coupled to body members 128.

Latch position indicator 123 includes an indicator body 133 coupled to handle member 122 intermediate a first end 136 and a second end 138. First end 136 of the handle member 122 is pivotably coupled to rocker arms 124 and the second end 138 includes a handle portion 139 accessible from a handle opening 141 in base 92, as shown in FIGS. 14–16. First end 136 includes a boss or lug 140 received in slots 142 formed in a second end 147 of rocker arms 124. A pivot pin, illustratively a shoulder screw 144, is provided to retain rocker arms 124 on boss 140. First end 136 of handle member 122 further includes a spring seat or mount 143, including a peg 145 having a cross-section in the shape of a plus-sign or cross and configured to be received by the end of a spring 146.

Spring 146 is positioned in a spring-receiving channel 148 defined by sidewalls 149 and end wall 150 of base 92. Spring 146 is positioned between spring seat 143 of handle member 122 and end wall 150 of base 92 to bias handle member 122 downwardly in the direction of arrow 152 in FIGS. 11, 13, 14, and 16. Because handle member 122 is biased in direction 152, pins 126 are biased outwardly into apertures 134, 135 in respective flanges 76, 118*b* of respective first links 66, 112. More particularly, with reference to FIGS. 11 and 14, downward movement of handle member 122 in the direction of arrow 152 causes the boss 140 and respective shoulder screws 144 to move downwardly the second ends 147 of the rocker arms 124*a*, 124*b*. Downward movement of the second ends 147 of the rocker arms 124*a*, 124*b* causes the rocker arms 124*a*, 124*b* to pivot about pivot pins 125, resulting in outward movement of the first ends 131 of the rocker arms 124*a*, 124*b* and, as such, pins 126*a* and 126*b*, in the direction of arrows 153*a* and 153*b*, respectively. When pins 126 are positioned in apertures 134, 135 of respective first link 66, 112, then fourth link 72 is coupled together with respective first link 66, 112 at two axially spaced apart locations. This essentially binds the fourth link 72 by preventing rotation of respective linkage assembly 62, 64 thereby preventing siderail 20, 22 from swinging to the lower position.

To unbind respective linkage assemblies 62, 64 and permit respective siderails 20, 22 to swing to the down position, latch pins 126 are moved from the latched position (FIGS. 11 and 14) to the unlatched position (FIGS. 12 and 15). A caregiver unlatches latch pins 126 by pulling upwardly on handle portion 139 of handle member 122 in the direction of arrow 154 and against the bias of spring 146. This upward movement of the handle member 122 causes the boss 140 and respective shoulder screw 144 to move upwardly the second ends 147 of the rocker arms 124. Upward movement of the second ends 147 of the rocker arms 124 causes the rocker arms 124 to pivot about pivot pins 125, resulting in inward movement of the first ends 131 of rocker arms 124*a* and 124*b*. As such, pins 126*a* and 126*b* move inwardly out of apertures 134, 135 of respective first link 66, 112 of linkage assembly 62, 64 in the direction of arrows 155*a* and 155*b*, respectively. Pins 126 no longer bind respective first link 66, 112 and respective fourth link 72.

FIG. 11 shows retainer 120 in a latched position that prevents vertical movement of respective siderails 20, 22. Latch pins 126 extend through apertures 134, 135 beyond respective flanges 76, 118*b* to bind the respective linkage assemblies 62, 64. FIG. 12 shows retainer 120 in an unlatched position that allows the movement of respective siderails 20, 22 between an up position and a down position. Pins 126 do not extend through apertures 134, 135 of flanges 76, 118*b* and therefore do not bind the respective linkage 62, 64. FIG. 13 shows the retainer 120 in a false latched position intermediate the positions of FIGS. 11 and 12, where pins 126 extend to and contact flanges 76, 118*b* but do not extend into apertures 134, 135 of flanges 76, 118*b*. In this position, the pins 126 do not bind the respective linkage assemblies 62, 64 and, in fact, may move or "ride" along an inwardly facing surface 151 of respective flanges 76, 118*b* as the siderail 20, 22 is vertically moved.

When respective first links 66, 112 and fourth links 72 are free to pivot relative to one another, then respective linkage assemblies 62, 64 are also unbound and free to permit siderails 20, 22 to swing between the upper and lower positions. According to alternative embodiments of the present disclosure, other retainers may be provided to hold the siderails 20, 22 in the upper position such as clasps, catches, locks, other latches, clamps, pins, bolts, bars, hasp, hooks, or other retainers known to those of ordinary skill in the art.

As shown in FIGS. 14–16, latch position indicator 123 provides a visual indication of the position of latch pins 126 and is configured to move along with latch pins 126. When axially aligned with apertures 134, 135 in respective flanges 78, 118*b*, spring 146 biases pins 126 to extend fully through the apertures 134, 135 in the latched condition as detailed above and as shown in FIG. 11. In the latched condition as shown in FIG. 14, an upper portion 157 of indicator body 133 is below or substantially flush with an upper surface 156 defining opening 121. FIG. 15 shows upper portion 157 of indicator body 133 above upper surface 156 in the fully unlatched condition when pins 126 are retracted from apertures 134, 135 and inwardly spaced from flanges 76, 118*b*, as shown in FIG. 12. FIG. 16 shows a partially unlatched or false latched condition, where pins 126 are positioned outside of apertures 134, 135 intermediate the latched condition of FIG. 11 and the fully unlatched condition of FIG. 12. More particularly as shown in FIG. 13, heads 132 of pins 126 rest against inside surfaces 151 of the respective flanges 76, 118*b* such that the pins 126 may move along flanges 76, 118*b* as a result of movement of the fourth link 72. The difference between the latched position shown in FIG. 11 and the false latched position shown in FIG. 12 is the distance that pins 126 extend toward respective apertures 134, 135. To indicate to the caregiver that the siderail 20, 22 is not in the latched condition, the upper portion 157 of indicator body 133 is outside the upper surface 156 of the body 92.

Figure 17:
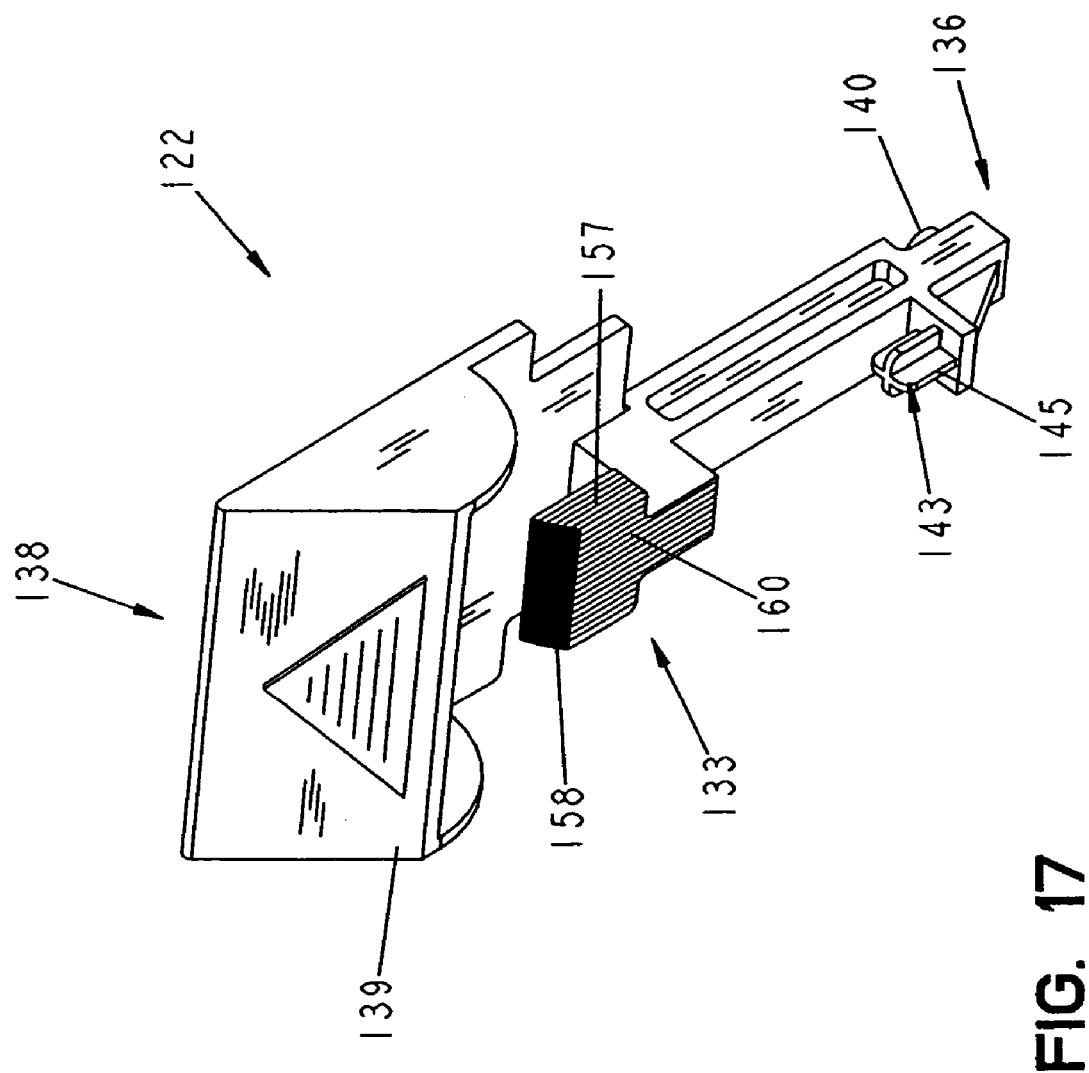
FIG. 17 is a perspective view of the handle member of the link of FIG. 10.

As shown in FIG. 17, indicator body 133 illustratively includes a plurality of surfaces, including a top surface 158 located on upper portion 157 of indicator body 133 and visible in the latched, unlatched and partially latched conditions of retainer 120. Side surfaces 160 are located below the plane of the top surface 158 and are hidden from view when retainer 120 is in the latched condition (FIG. 14). Side surfaces 160 are visible when retainer 120 is in the fully unlatched and partially unlatched conditions (FIGS. 15 and 16). In an illustrated embodiment, side surfaces 160 and top surface 158 are of visibly distinguishable, and illustratively include different colors or designs. For example, top surface 158 may be green in color, while side surfaces 160 may be red in color. Alternatively, top surface 158 may be non-reflective, while side surfaces 160 may be reflective. While illustratively, side surface 160 contrasts with top surface 158, any color scheme or design for top surface 158 and side surfaces 160 may be utilized for the latch position indicator 123.

In a further illustrative embodiment, an electronic latch detector 170 may be associated with retainer 120 and is configured to provide a signal to control system 45 (FIG. 4). More particularly, latch detector 170 provides a signal to control system 45 when retainer 120 is in the fully latched position of FIGS. 11 and 14. Illustratively, latch detector 170 may comprise a conventional limit switch supported by base 92 and including a lever arm configured to be depressed only when handle member 122 is in its latched position. Alternatively, latch detector 170 may comprise any other suitable sensor including, but not limited to, a magnet and a Hall effect sensor of the type detailed above in connection with siderail position detector 57. Absent a signal from latch detector 170, control system 45 activates a latch light 172 providing a visual indication to the caregiver that retainer 120 is not fully latched. It should be appreciated that latch light 172 may comprise any conventional lamp, including a dual color lamp. Alternatively, latch light 172 may be replaced with another suitable indicator, such as an audible alarm.

It should be appreciated that latch position indicator 123 and electronic latch detector 170 may be configured for use in connection with devices other than hospital beds where an indication of a positive or full latching condition is required.

Figure 18:
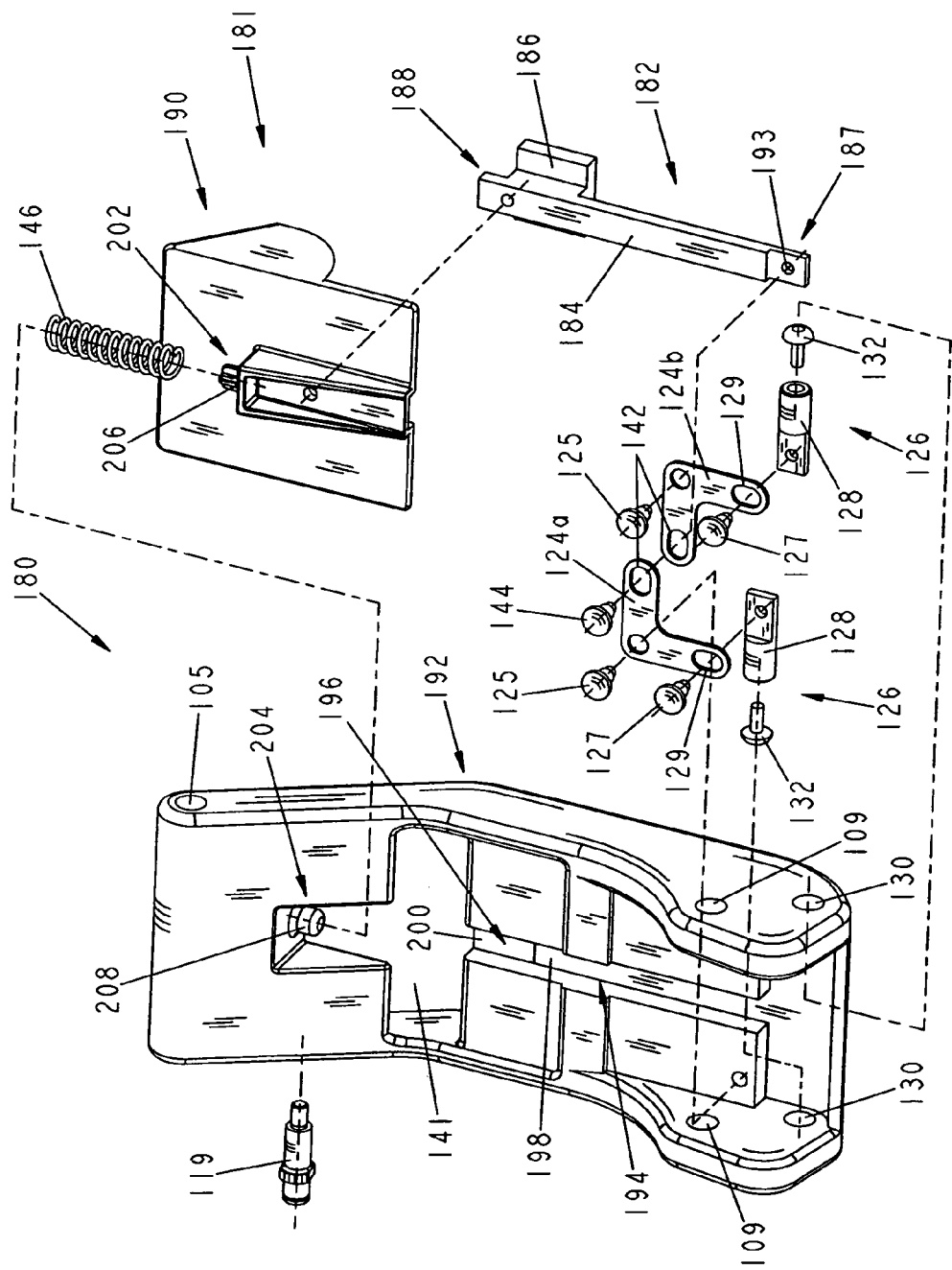
FIG. 18 is an exploded rear perspective of a link similar to FIG. 10 including an alternative embodiment latch.
Figure 19:
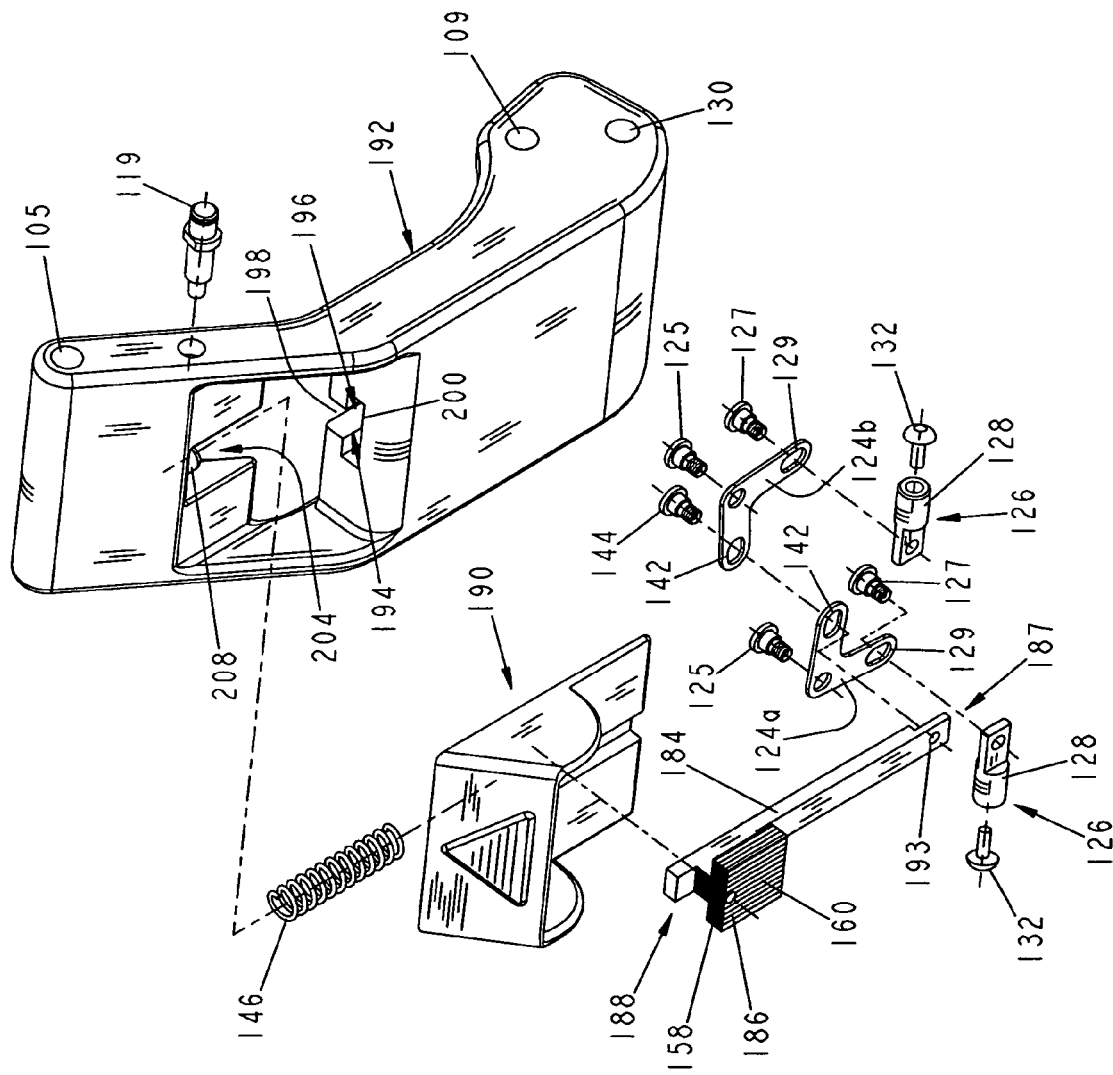
FIG. 19 is an exploded front perspective view of the link of FIG. 18 including the alternative embodiment latch.

Alternative embodiments of fourth link 180 and handle member 181 are shown in FIGS. 18 and 19. In the following description of handle member 181, like components are identified with the same reference numbers as described above with respect to fourth link 72. Handle member 181 includes a latch indicator 182, comprising a bar 184 coupled to an indicator body 186. A first end 187 of the bar 184 is pivotably coupled to rocker arms 124 and a second end 188 of the bar 184 is coupled to a handle portion 190. A pivot pin, illustratively a shoulder screw 144 is positioned in slots 142 formed in rocker arms 124 and is threadably received by an aperture 193 formed in the first end 187 of bar 184. The base 192 includes an elongated slot 194 including an upper portion 196 configured to receive indicator body 186. Upper portion 196 has a substantially T-shaped cross-section having a first portion 198 configured to slidably receive bar 184 and a second portion 200 configured to slidably receive indicator body 186.

Handle member 190 is accessible from handle opening 141 in base 192. Spring 146 biases the handle member 190 downwardly and is received intermediate a first spring seat 202 coupled to the handle portion 190 and a second spring seat 204 coupled to the base 192. First spring seat 202 includes a first peg 206 having a cross-section in the shape of a plus-sign or cross and configured to be received by a first end of spring 146. Second spring seat 204 includes a second substantially cylindrical peg 208 configured to be received by a second end of spring 146. In operation, sliding movement of handle member 181 causes pivoting movement of rocker arms 124 and subsequent movement of the pins 126 in a direction substantially perpendicular to the movement of handle member 181. As such, operation of handle member 181 with respect to rocker arms 124 and pins 126 is substantially similar to that with respect to the above illustrative embodiment handle member 122.

While the above described embodiments describe rocker arms 124 for transmitting movement of handle member 190 to movement of pins 126, it should be appreciated that substitutions may be made therefore, including the use of rack and pinions, gears, and hooks.

Although the invention has been described in detail with reference to certain preferred embodiments, variations and modifications exist within the spirit and scope of the invention as described and defined in the following claims.

The invention claimed is:

1. A patient support comprising,
a frame;
a siderail supported by the frame, the siderail including a rail member, a linkage configured to permit vertical movement of the rail member between a raised position and a lowered position, and a latching mechanism configured to retain the rail member in at least one of the raised position and the lowered position; and
the latching mechanism including a rocker arm having first and second ends movable about a pivot axis, a handle member coupled proximate the first end of the rocker arm, a latch member coupled proximate the second end of the rocker arm, the handle member being configured to pivot the rocker arm about the pivot axis such that the rocker arm moves the latch member between a latched position which prevents vertical movement of the rail member and an unlatched position which permits vertical movement of the rail member, wherein the handle member is configured to slide along a linear path to provide pivoting movement of the rocker arm.

2. The patient support of claim 1, wherein linear movement of the handle member in a first direction causes linear movement of the latch member in a second direction not parallel to the first direction.

3. A patient support comprising,
a siderail supported by the frame, the siderail including a rail member, a linkage configured to permit vertical movement of the rail member between a raised position and a lowered position, and a latching mechanism configured to retain the rail member in at least one of the raised position and the lowered position; and
the latching mechanism including a rocker arm having first and second ends movable about a pivot axis, a handle member coupled proximate the first end of the rocker arm, a latch member coupled proximate the second end of the rocker arm, the handle member being configured to pivot the rocker arm about the pivot axis such that the rocker arm moves the latch member between a latched position which prevents vertical movement of the rail member and an unlatched position which permits vertical movement of the rail member wherein the linkage includes a link having a base configured to support the latching mechanism and defining a handle opening, and the handle member includes a first end pivotably coupled to the rocker arm and a second end accessible from the handle opening.

4. The patient support of claim 3, further comprising a spring positioned intermediate the first end of the handle member and the base of the link, the spring being configured to bias the handle member such that the latch member is in the latched position.

5. A patient support comprising
a siderail supported by the frame, the siderail including a rail member, a linkage configured to permit vertical movement of the rail member between a raised position and a lowered position, and a latching mechanism configured to retain the rail member in at least one of the raised position and the lowered position; and
the latching mechanism including a rocker arm having first and second ends movable about a pivot axis, a handle member coupled proximate the first end of the rocker arm, a latch member coupled proximate the second end of the rocker arm, the handle member being configured to pivot the rocker arm about the pivot axis such that the rocker arm moves the latch member between a latched position which prevents vertical movement of the rail member and an unlatched position which permits vertical movement of the rail member wherein the linkage includes a first link coupled to the frame, a second link pivotably coupled to the first link, a third link pivotably coupled to the second link, and a fourth link pivotably coupled to the third link and the first link, the latch member in the latched position being configured to bind the fourth link and the first link to prevent pivoting movement therebetween.

6. A patient support comprising
a siderail supported by the frame, the siderail including a rail member, a linkage configured to permit vertical movement of the rail member between a raised position and a lowered position, and a latching mechanism configured to retain the rail member in at least one of the raised position and the lowered position; and
the latching mechanism including a rocker arm having first and second ends movable about a pivot axis, a handle member coupled proximate the first end of the rocker arm, a latch member coupled proximate the second end of the rocker arm, the handle member being configured to pivot the rocker arm about the pivot axis such that the rocker arm moves the latch member between a latched position which prevents vertical movement of the rail member and an unlatched position which permits vertical movement of the rail member wherein the linkage includes a flange coupled to the frame and including a latch aperture, a link pivotably supported by the flange and coupled to the latch member, the latch member being received within the latch aperture when in the latched position to prevent pivoting movement of the link.

7. A patient support comprising
a siderail supported by the frame, the siderail including a rail member, a linkage configured to permit vertical movement of the rail member between a raised position and a lowered position, and a latching mechanism configured to retain the rail member in at least one of the raised position and the lowered position;
the latching mechanism including a rocker arm having first and second ends movable about a pivot axis, a handle member coupled proximate the first end of the rocker arm, a latch member coupled proximate the second end of the rocker arm, the handle member being configured to pivot the rocker arm about the pivot axis such that the rocker arm moves the latch member between a latched position which prevents vertical movement of the rail member and an unlatched position which permits vertical movement of the rail member;
an indicator operably coupled to the latch member and configured to provide a visual indication of the unlatched position wherein the indicator includes an indicating surface configured to move in response to movement of the latch member wherein the linkage includes a link having a base configured to receive the latching mechanism and defining an indicator opening; and
the indicator is fixed to the handle member and is configured to move relative to the indicator opening such that the indicating surface is visible when the latch member is in the unlatched position and is substantially hidden by the base when the latch member is in the latched position.

8. A patient support comprising:
a frame;
a siderail supported by the frame, the siderail including a rail member, a linkage configured to permit vertical movement of the rail member between a raised position and a lowered position, and a latching mechanism configured to retain the rail member in at least one of the raised position and the lowered position; and
the latching mechanism including a latch member configured to move between a latched position which prevents vertical movement of the rail member and an unlatched position which permits vertical movement of the rail member, and a handle member operably coupled to the latch member and configured to provide movement of the latch member between the latched position and the unlatched position, wherein movement of the handle member in a first plane causes movement of the latch member in a second plane not parallel to the first plane wherein the latching mechanism includes a pair of latch members configured to move toward each other during movement from the latched position to the unlatched position, and configured to move away from each other during movement from the unlatched position to the latched position.

9. A patient support comprising:
a frame;
a siderail supported by the frame, the siderail including a rail member, a linkage configured to permit vertical movement of the rail member between a raised position and a lowered position, and a latching mechanism configured to retain the rail member in at least one of the raised position and the lowered position; and
the latching mechanism including a latch member configured to move between a latched position which prevents vertical movement of the rail member and an unlatched position which permits vertical movement of the rail member, and a handle member operably coupled to the latch member and configured to provide movement of the latch member between the latched position and the unlatched position, wherein movement of the handle member in a first plane causes movement of the latch member in a second plane not parallel to the first plane wherein the latching mechanism includes a rocker arm having first and second ends movable about a pivot axis, the handle member being coupled to the first end of the rocker arm, the latch member being coupled to the second end of the rocker arm, and the handle member being configured to pivot the rocker arm about the pivot axis such that the rocker arm moves the latch member between the latched position and the unlatched position.

10. The patient support of claim 9, wherein the rocker arm is substantially L-shaped.

11. A patient support comprising:
a frame;
a siderail supported by the frame, the siderail including a rail member, a linkage configured to permit vertical movement of the rail member between a raised position and a lowered position, and a latching mechanism configured to retain the rail member in at least one of the raised position and the lowered position; and
the latching mechanism including a latch member configured to move between a latched position which prevents vertical movement of the rail member and an unlatched position which permits vertical movement of the rail member, and a handle member operably coupled to the latch member and configured to provide movement of the latch member between the latched position and the unlatched position, wherein movement of the handle member in a first plane causes movement of the latch member in a second plane not parallel to the first plane wherein the handle member is configured to slide along a linear path to provide linear movement of the latch member.

12. A patient support comprising:

a frame;

a siderail supported by the frame, the siderail including a rail member, a linkage configured to permit vertical movement of the rail member between a raised position and a lowered position, and a latching mechanism configured to retain the rail member in at least one of the raised position and the lowered position; and the latching mechanism including a latch member configured to move between a latched position which prevents vertical movement of the rail member and an unlatched position which permits vertical movement of the rail member, and a handle member operably coupled to the latch member and configured to provide movement of the latch member between the latched position and the unlatched position, wherein movement of the handle member in a first plane causes movement of the latch member in a second plane not parallel to the first plane wherein the linkage includes a flange coupled to the frame and including a latch aperture, a link pivotably supported by the flange and coupled to the latch member, the latch member being received within the latch aperture when in the latched position to prevent pivoting movement of the link.

13. A patient support comprising a frame;

a siderail supported by the frame, the siderail including a rail member, a linkage configured to permit raising and lowering of the rail member, and a retaining member configured to retain the rail member in the at least one of the raised position and the lowered position; and means for moving the retaining member between a first position which prevents raising and lowering of the rail member and a second position which permits raising and lowering of the rail member, wherein movement of the means for moving in a first direction causes linear movement of the retaining member in a second direction not parallel to the first direction wherein the means for moving includes a rocker arm having first and second ends movable about a pivot axis, a handle member coupled to the first end of the rocker arm, and the retaining member being coupled to the second end of the rocker arm, wherein the means for moving is configured to rotate the rocker arm about the pivot axis such that the rocker arm moves the retaining member between the first position and the second position.

14. The patient support of claim 13, wherein the handle member is configured to slide along a linear path to provide linear movement of the retaining member.

15. A patient support comprising a frame;

a siderail supported by the frame, the siderail including a rail member, a linkage configured to permit raising and lowering of the rail member, and a retaining member configured to retain the rail member in the at least one of the raised position and the lowered position; and means for moving the retaining member between a first position which prevents raising and lowering of the rail member and a second position which permits raising and lowering of the rail member, wherein movement of the means for moving in a first direction causes linear movement of the retaining member in a second direction not parallel to the first direction wherein the linkage comprises a flange coupled to the frame and including an aperture, a link pivotably supported by the flange and coupled to the retaining member, the retaining member being received within the aperture when in the first position to prevent pivoting movement of the link.

* * * * *